US012780891B2

(12) United States Patent
Lin et al.

(10) Patent No.: US 12,780,891 B2
(45) Date of Patent: Nov. 3, 2026

(54) MIXTURE OF INTERFERON ALPHA 2B WITH MODIFIED SEQUENCES THEREOF

(71) Applicant: PharmaEssentia Corporation, Taipei (TW)

(72) Inventors: Ko-Chung Lin, Lexington, MA (US); Ming-Pin Hsu, Taipei (TW); Yu-Kuei Tsai, Taipei (TW); Yi-Te Yo, Taipei (TW); Jiing-Guang Chuang, Taipei (TW); Shin-Jye Lee, Taipei (TW)

(73) Assignee: PharmaEssentia Corporation, Taipei (TW)

( * ) Notice: Subject to any disclaimer, the term of this patent is extended or adjusted under 35 U.S.C. 154(b) by 0 days.

(21) Appl. No.: 19/361,604

(22) Filed: Oct. 17, 2025

(65) Prior Publication Data

US 2026/0109750 A1 Apr. 23, 2026

Related U.S. Application Data

(60) Provisional application No. 63/709,791, filed on Oct. 21, 2024, provisional application No. 63/709,800, filed on Oct. 21, 2024, provisional application No. 63/709,808, filed on Oct. 21, 2024.

(51) Int. Cl.
*C07K 14/56* (2006.01)
*A61K 38/00* (2006.01)
*C12P 21/02* (2006.01)
*G01N 33/68* (2006.01)

(52) U.S. Cl.
CPC .............. *C07K 14/56* (2013.01); *C12P 21/02* (2013.01); *G01N 33/6824* (2013.01); *A61K 38/00* (2013.01)

(58) Field of Classification Search
None
See application file for complete search history.

(56) References Cited

U.S. PATENT DOCUMENTS 5,382,657 A 1/1995 Karasiewicz et al.
5,643,575 A 7/1997 Martinez et al.
5,738,846 A 4/1998 Greenwald et al.
5,824,784 A 10/1998 Kinstler et al.
5,919,455 A 7/1999 Greenwald et al.
5,932,462 A 8/1999 Harris et al.
5,951,974 A 9/1999 Gilbert et al.
6,824,768 B2 11/2004 Stalgis et al.
7,125,843 B2 10/2006 DeFrees et al.
7,731,948 B2 6/2010 Samaritani et al.
8,106,160 B2 1/2012 Wu et al.
8,143,214 B2 3/2012 Lin
8,273,343 B2 9/2012 Lin
8,617,532 B2 12/2013 Lin et al.
11,559,567 B2 1/2023 Klade et al.
2004/0136952 A1 7/2004 Bhaskaran et al.
2005/0009988 A1 1/2005 Harris et al.
2005/0107277 A1 5/2005 Lin et al.
2005/0143292 A1 6/2005 DeFrees et al.
2005/0266465 A1 12/2005 Patten et al.
2006/0057070 A1 3/2006 Assaly et al.
2006/0166932 A1 7/2006 Zeldis
2007/0185135 A1 8/2007 Wu et al.
2009/0035273 A1 2/2009 Liu
2009/0053177 A1 2/2009 Lin
2009/0263355 A1 10/2009 Furuya et al.
2009/0269306 A1 10/2009 Wu et al.
2009/0311216 A1 12/2009 Johnson-Jackson et al.
2011/0262380 A1 10/2011 Lin et al.
2012/0310140 A1 12/2012 Kramer et al.
2021/0230291 A1 7/2021 Kley et al.
2023/0096991 A1 3/2023 Lin
2025/0101484 A1 3/2025 Lin et al.

FOREIGN PATENT DOCUMENTS

CN 1966547 A 5/2007
CN 1970572 A 5/2007
CN 101002944 A 7/2007
CN 101104078 A 1/2008
CN 101108895 A 1/2008
CN 101491682 A 7/2009
CN 101514229 A 8/2009
CN 101671390 A 3/2010
CN 116240253 A 6/2023
EP 0809996 A2 12/1997
EP 1834963 A1 9/2007
JP 2003513681 A 4/2003
JP 2003527090 A 9/2003
(Continued)

OTHER PUBLICATIONS

Bewersdorf et al., "Interferon therapy in myelofibrosis—a systematic review and meta-analysis" Clin Lymphoma Myeloma Leuk. (Year: 2020).*
Breccia, "Interferon in chronic myeloid leukaemia: is it useful for treatment-free remission?" British Journal of Haematology (Year: 2023).*
Gu et al., "Clinical outcomes of interferon therapy for polycythemia vera and essential thrombocythemia: a systemmatic review and meta-analysis" International Journal of Hematology (Year: 2021).*
Liao et al., "Removal of N-terminal methionine from recombinant proteins by engieered *E. coli* methionine aminopeptidase" Protein Science (Year: 2004).*
(Continued)

*Primary Examiner* — Tracy Vivlemore
*Assistant Examiner* — John David Moore
(74) *Attorney, Agent, or Firm* — Singleton Law, PLLC; Chainey P. Singleton

(57) ABSTRACT

A composition and a new method of manufacturing and producing such composition including modified interferon alpha 2 b with modified Nle substituted, Gly at position 45 substituted to Asp and/or Asn at position 66 substituted to Lys substituted modified interferon alpha 2 b, and/or a mixture thereof is disclosed herein.

3 Claims, 6 Drawing Sheets

Specification includes a Sequence Listing.

(56) References Cited

FOREIGN PATENT DOCUMENTS

| | | | | |
|---|---|---|---|---|
| JP | 2005525302 | A | 8/2005 | |
| JP | 2013513611 | A | 4/2013 | |
| WO | 2004022630 | A3 | 4/2004 | |
| WO | 2005000359 | A2 | 1/2005 | |
| WO | 2006024953 | A3 | 3/2006 | |
| WO | 2006084089 | A2 | 8/2006 | |
| WO | 2006094530 | A1 | 9/2006 | |
| WO | 2006095029 | A2 | 9/2006 | |
| WO | 2006095029 | A3 | 11/2006 | |
| WO | 2009023826 | A1 | 2/2009 | |
| WO | 2009030065 | A1 | 3/2009 | |
| WO | 2009030066 | A1 | 3/2009 | |
| WO | WO-2009046080 | A1 * | 4/2009 | ............. A61P 31/12 |
| WO | 2010014874 | A2 | 2/2010 | |
| WO | 2010014874 | A3 | 2/2010 | |
| WO | 2011072138 | A2 | 6/2011 | |
| WO | 2013058762 | A1 | 4/2013 | |

OTHER PUBLICATIONS

Wang et al., “Improving the expression of recombianant proteins in *E. coli* BL21 (De3) under Acetate stress: an alkaline pH shift approach” PLos One (Year: 2014).*
Heyde, “Tailoring the evolution of BI21(DE3) uncovers key role for RNA stability in gene expression toxicity” Communications Biology (Year: 2021).*
Stosch, “Hybrid modeling as QbD/PAT tool in process development: an industrial *E. coli* case study” Bioprocess Biosyst Eng (Year: 2016).*
International Search Report and Written Opinion dated Feb. 20, 2026; pp. 1-17.
International Search Report and Written Opinion dated Feb. 4, 2026, pp. 1-12.
Ni et al.; “Investigation into the disincorporation of norleucine into a recombinant protein vaccine candidate”; J Ind Microbial Biotechnol (2015) 42:971-975.
Proud-PV “Polycythemias Vera”, pp. 1-2, retrieved Jun. 8, 2021.
Proud-PV “The Study Drugs” pp. 1-2, retrieved Apr. 15, 2015.
Proud-PV; “The Proud-PV Study”; pp. 1-5; retrieved Jun. 8, 2021.
Quintas-Cardama et al.; “Pegylated Interferon Alfa-2a Yields High Rates of Hematologic and Molecular Response in Patients With Advanced Essential Thrombocythemia and Polycythemia Vera”; Journal of Clinical Oncology, vol. 27, pp. 5418-5424, 2009.
Radygina et al.; “Diseases caused by human T-lymphotropic virus type 1 (HTLV-1)”; Microbiology Independent Research Journal, vol. 11, No. 1, 2024; pp. 57-69.
Ramassamy et al.; “Adult T-cell leukemia/lymphoma incidence rate in French Guiana: a prospective cohort of women infected with HtLV-1”; The American Society of Hematology, vol. 4, No. 9, May 12, 2020, pp. 2044-2048.
Roberts et al.; “Chemistry for Peptide and Protein PEGylation”; Advanced Drug Delivery Reviews, vol. 54, pp. 459-476, 2002.
Samuelsson et al.; “A Phase II Trial of Pegylated Interferon α-2b Therapy for Polycythemia Vera and Essential Thrombocythemia”; Cancer vol. 106, pp. 2397-2405; 2006.
Schinzel et al.; “The phosphate recognition site of *Escherichia coli* maltodextrin phosphorylase”; Federation of European Biochemical Societies vol. 286, pp. 125-128, 1991.
Sever et al.; “Therapeutic options for patients with polycythemia vera and essential thrombocythemia refractory/resistant to hydroxyurea”; Leukemia and Lymphoma Early Online, pp. 1-6, 2014.
Shah et al.; “Epidemiology and survival trend of Adult T-cell Leukemia/Lymphoma in the United States”; Cancer, Feb. 1, 2020; 126(3): 567-574.
Sigma Genosys; “Designing Custom Peptides” pp. 1-2, retrieved Dec 16, 2014.
Stahl et al.; “Management of myelofibrosis: JAK inhibition and beyond”; Expert Review of Hematology accepted article preview, pp. 1-66, 2017.
Sun et al.; “Use of Ropeginterferon Alfa-2b in Adult T-Cell Leukemia/Lymphoa: A Case Report”; MPN Asia 2025, p. 1.
Umekita et al.; “HTLV-1 Infection and Rheumatic Diseases”; Frontiers in Microbiology, vol. 11, Article 152, Feb. 2020; pp. 1-7.
Vannucchi et al.; “JAK2 allele burden in the myeloproliferative neoplasms: effects on phenotype, prognosis and change with treatment”; Therapeutic Advances in Hematology vol. 2, pp. 21-32, 2011.
Vannucchi et al.; “Ruxolitinib reduces JAK2 p.V617F allele burden in patients with polycythemia vera enrolled in the Response study”; Annals of Hematology vol. 96, pp. 1113-1120, 2017.
Verger et al.; “Ropeginterferon alpha-2b targets JACK2V617F-positive polycythemia vera cells in vitro and in vivo”; Blood Cancer Journal vol. 8, pp. 1-6, 2018.
Voet et al.,; “Abnormal Hemoglobins”; Biochemistry, pp. 235-241, 1995.
Webster et al.,; PEGylation of somatropin (recombinant human growth hormone): Impact on its clearance in humans; Xenobiotica Vo.. 38, pp. 1340-1351, 2008.
Yuen et al.; “Suppression of Type I Interferon Production by Human T-Cell Leukemia Virus Type 1 Oncoprotein Tax through Inhibition of IRF3 Phosphorylation”; Journal of Virology, vol. 90, No. 8, Apr. 2016, pp. 3902-2912.
Zalipsky; “Chemistry of Polyethylene Glycol Conugates with Biologically Active Molecules”; Advanced Drug Delivery Reviews Vo. 16, pp. 157-182, 1995.
Zhang et al.; “Interferon Alpha 2b for Treating Patients with JAK2V617F Positive Polycythemia Vera and Essential Thrombocytosis”; Asian Pacific Journal of Cancer Prevention vol. 15, pp. 1681-1684, 2014.
International Search Report and Written Opinion dated Apr. 2, 2026, pp. 1-14.
AOP Orphan Pharmaceuticals Announces Progress of Pivotal Phase III Trial Proud-PV of Novel Mono-Pegylated Interferon Alpha 2B for the Treatment of Polycythemia Vera; AOP Orphan, Jul. 10, 2013.
AOP Orphan Pharmaceuticals Reports Positive Phase II Data of Novel Mono-Pegylated Interferon Alpha 2B for Treatment of Polycythemia Vera (PV); AOP Orphan; Dec. 10, 212.
Arnason; “Long-Term Experience with Interferon Beta-1b (Betaferon) in Multiple Sclerosis”; Journal of Neurology vol. 252, pp. 28-33, 2005.
Bailon et al.; “Rational Design of a Potent, Long-Lasting Form of Interferon: A 40 kDa Branched Polyethylene Glycol-Conjugated Interferon α-2a for the Treatment of Hepatitis C”; Bioconjugate Chemistry vol. 12, pp. 195-202, 2001.
Baker et al.; “N-Terminally PEGylated Human Interferon-β-1a with Improved Pharmacokinetic Properties and in Vivo Efficacy in a Melanoma Angiogenesis Model” Bioconjugate Chemistry vol. 17, pp. 179-188, 2006.
Barosi et al.; “JAK4617F allele burden ≥50% is associated with response to ruxolitinib in persons with MPN-associated myelofibrosis and splenomegaly requiring therapy”; Leukemia accepted article preview, pp. 1-16, 2016.
Basu et al.; “Structure-Function Engineering of Interferon-β-1b for Improving Stability, Solubility, Potency, Immunogenicity, and Pharmacokinetic Properties by Site-Selection Mono-PEGylation”; Bioconjugate Chemistry vol. 17, pp. 618-630, 2006.
Berendsen; “A Glimpse of the Holy Grail?”; Science vol. 282, pp. 645-643, 1998.
Bjorn et al.; “Combination therapy with interferon and JAK1-2 inhibitor is feasible: Proof of concept with rapid reduction in JAK2V617F-allele burden in polycythemia vera”; Leukemia Research Reports vol. 3, pp. 73-75, 2014.
Booklet on Current Information on HTLV-1 and HAD; Japanese Red Cross Kyushu Block Blood Center, 2020, pp. 1-20.
Bradley et al.; “Limits of Cooperatively in a Structurally Modular Protein: Response of the Notch Ankyrin Domain to Analogous Alanine Substitutions in Each Repeat”; Journal of Molecular Biology vol. 324, pp. 373-386, 2002.
Cachat et al.; “Alpha Interferon Restricts Human T-Lymphotropic Virus Type 1 and 2 De Novo Infection through PKR Activation”; Journal of Biology, vol. 87, No. 24, Dec 2013, pp. 13386-13396.

(56) References Cited

OTHER PUBLICATIONS

Castro, Leonor S. et al.; "Interferon-Based Biopharmaceuticals: Overview on the Production, Purification, and Formulation"; Vaccines 2021, 9, 328; pp. 1-51.

clinicaltrails.gov "History of Changes for Study NCT02218047"; pp. 1-6, retrieved Jun. 13, 2018.

Deininger et al.; "The effect of long-term ruxolitinib treatment on JAK2p.V617F allele burden in patients with myelofibrosis"; Blood vol. 126, pp. 1551-1554, 2015.

dictionary.com; "Moiety"; pp. 1-3, retrieved Mar. 12, 2010.

Dixon et al.; "Imaging Spectrum of HTLV-1-Related Neurologic Disease"; The American Academy of Neurology, Clinical Practice 2023; pp. 1-10.

Einsiedel et al.; "Human T-cell leukaemia virus type 1 associated pulmonary disease: clinical and pathological features of an under-recognized complication of HTLV-1 infection"; Retrovirology (2021) 18:1, pp. 1-13.

European Medicines Agency; "Public Summary of Opinion on Orphan Designation"; pp. 1-4, Dec 20, 2011.

Extended European Search Report dated Dec. 20, 2023, pp. 1-13.

Gao, Chun-Hui et al.; "The initial inoculation ratio regulates bacterial coculture interactions and metabolic capacity"; The ISME Journal (2021) 15:29-40.

Gissliner et al.; "Ropeginterferon alfa-2b versus standard therapy for polycythaemia vera (Proud-PV and Continuation-PV): a randomised, non-inferiority, phase 3 trial and its extension study", Lancet Haematol 2020; vol. 7, 7:e196-e208, Mar. 2020.

Gisslinger et al.; "Ropeginterferon alfa-2b versus standard therapy for polycythemia vera (Proud-PV and Continuation-PV): a randomized, non-inferiority, phase 3 trial and its extension study"; Lancet Hematology, pp. 1-13, 2020.

Gisslinger et al.; "Ropeginterferon alfa-2b, a novel IFNα-2b, induces high response rates with low toxicity in patients with polycythemia vera"; Blood vol. 126, pp. 1762-1769, 2015.

Gupta et al.; "A phase 1/2, open-label study evaluating twice-daily administration of momelotinib in myelofibrosis"; Haematologica vol. 102, pp. 94-102, 2017.

Hsu et al.; "Ropeginterferon Alfa-2b administered every two weeks for patients with genotype 2 chronic hepatitis C"; Journal of the Formosan Medical Association vol. 120, pp. 956-964, 2021.

Huang et al.; "Real-world experience with Ropeginterferon-alpha 2b (Besremi) in Philadelphia-negative myeloproliferative neoplasms", Journal of the Formosan Medical Association (2021) 120; pp. 863-873.

Huang et al.; "Ropeginterferon alfa-2b every 2 weeks as a novel pegylated interferon for patients with chronic hepatitis B"; Hepatology International vol. 14, pp. 97-1006, Oct. 24, 2020.

Ianotto et al.; "Benefits and pitfalls of pegylated interferon-α2a therapy in patients with myeloproliferative neoplasm-associated myelofibrosis: a French Intergroup of Myeloprolierative neoplasms (FIM) study"; Haematologica vol. 103, pp. 438-446, 2018.

Ianotto et al.; "PEG-FN-α-2a therpy in patients with myelofibrosis"; British Journal of Hematology vol. 46, pp. 218-230, 2009.

International Search Report and Written Opinion dated Feb. 4, 2025, pp. 1-15.

Kato et al.; "Nationwide Hospital-Based Survey of Adult T-Cell Leukemia/Lymphoma in Japan"; Viruses 2022, 14, 791, pp. 1-8.

Kiladjian et al.; "High molecular response rate of polycythemia vera patients treated with pegylated interferon α-2a"; Blood vol. 108, pp. 2037-2040, 2006.

Kiladjian et al.; "Interferon-alpha for the therapy of myeloproliferative neoplasms: Targeting the malignant clone"; Leukemia accepted article preview, pp. 1-21, 2015.

Kiladjian et al.; "Pegylated interfereon-alia-2a induces complete hematologic and molecular responses with low toxicity in polycythemia vera"; Blood, Oct. 15, 2008, vol. 112 No. 8, pp. 3065-3072.

Kiladjian et al.; "Thromboembolic Risk Reduction and High Rate of Complete Molecular Response with Long-Term Use of Ropeginterferon Alpha-2b in Polycythemia Vera: Results from a Randomized Controlled Study"; Blood vol. 134, Supplement 1, pp. 1-4, 2019.

Langer et al.; "Pegylated interferon for the treatment of high risk essential thrombocythemia: results of a phase II study"; Haematologica vol. 90, pp. 1333-1338, 2005.

Lee et al.; "Efficacy and Safety of Ropeginterferon Alfa-2b in Low-Risk Polycythemia Vera"; Korean Cancer Associate, Cancer Research and Treatment (CRT); Jun. 26, 2025; pp. 1-29.

Li et al.; "Synthesis of Polyethylene Glycol (PEG) Derivatives and PEGylated-Peptide Biopolymer Conjugates"; Biomacromolecules vol. 4, pp. 1055-1067, 2003.

Li, Xiangyu et al.; "An Online Respiratory Quotient-Feedback Strategy of Feeding Yeast Extract for Efficient Arachidonic Acid Production by Mortierella alpina"; Frontiers in Bioengineering and Biotechnology, vol. 5, Article 83, Jan. 2018, pp. 1-11.

Lin et al.; "Pharmaessentia Corp." The Ninth Annual BioAsia International Conference, Company Profiles, p. 1.

Martin et al.; "Human T-cell leukemia virus type 1 and Adult T-cell leukaemia/lymphoma in Queensland, Australia: a retrospective cross-section study"; Sex Trans Infect 2023; 99:50-52.

Masarova et al.; "A multicenter study to assess efficacy, safety, and tolerability of ropeginterferon alfa-2b-njft in patients with essential thrombocythermia in the US and CanadaL Exceed-ET trial"; Frontiers in Medicine; Apr. 17, 2025; pp. 1-8.

Masarova et al.; "Efficacy and safety of pegylated interferon alpha-2a in patients with essential thrombocythemia (ET) and polycythemia vera (PV): results of a phase 2 study after a 7-year median follow-up"; Lancet Hematology vol. 4, pp. e165-e175, 2017.

Mesa; "Highlights in Myeloproliferative Neoplasms From the 60th American Society of Hematology Annual Meeting"; Clinical Advances in Hematology and Oncology vol. 17, Supplement 2, pp. 1-20, 2019.

Mickle et al.; "Genotype-phenotype relationships in cystic fibrosis"; Medical Clinics of North America, vol. 84, No. 3, May 2000; pp. 597-607.

Miura et al.; "Current Perspectives in Human T-Cell Leukemia Virus Type 1 Infection and Its Associated Diseases"; Frontiers in Medicine, vol. 9, Article 867474, Apr. 2022, pp. 1-10.

Nell et al.; "Epidemiology of Adult T-Cell Leukaemia/Lymphoma in South Africa over a 10-Year Period"; Journal of Cancer Epidemiology, vol. 2022, Article ID 2058280, Aug. 31, 2022, pp. 1-5.

Ngo et al.; "Computational Complexity, Protein Structure Prediction, and the Levinthal Paradox"; The Protein Folding Problem and Tertiary Structure Prediction, pp. 491-495, 1994.

Pai et al.; "Long-acting interferon for myeloproliferative neoplasms—an update"; Expert Review of Hematology vol. 9, pp. 915-917, 2016.

Bandi et al.; "2D NMR Analysis of the Effect of Asparagine Deamidation Versus Methionine Oxidation on the Structure, Stability, Aggregation, and Function of a Therapeutic Protein"; American Chemical Society, Molecular Pharmaceutics 2019, 16, 4621-4635.

* cited by examiner

CDLPQTHSL GSRRTLMLLA QMRRISLFSC LKDRHDFGFP QEEFGNQFQK
AETIPVLHEM IQQIFNLFST KDSSAAWDET LLDKFYTELY QQLNDLEACV
IQGVGVTETP LMKEDSILAV RKYFQRITLY LKEKKYSPCA WEVVRAEIMR
SFSLSTNLQE SLRSKE (SEQ ID NO:1)

Figure 1

PCDLPQTHSL GSRRTLMLLA QMRRISLFSC LKDRHDFGFP QEEFGNQFQK
AETIPVLHEM IQQIFNLFST KDSSAAWDET LLDKFYTELY QQLNDLEACV
IQGVGVTETP LMKEDSILAV RKYFQRITLY LKEKKYSPCA WEVVRAEIMR
SFSLSTNLQE SLRSKE (SEQ ID NO:2)

Figure 2

MIXTURE OF INTERFERON ALPHA 2B WITH MODIFIED SEQUENCES THEREOF

CROSS-REFERENCE TO RELATED APPLICATIONS

The present application claims the benefit to U.S. Provisional Patent Application Ser. No. 63/709,791, U.S. Provisional Patent Application Ser. No. 63/709,800, and U.S. Provisional Patent Application Ser. No. 63/709,808, all of which filed on Oct. 21, 2024. The content of all of which are incorporated herein by reference in its entirety.

SEQUENCE LISTING

This application is being filed electronically via EFS-Web and includes an electronically submitted sequence listing in .xml format in ST.26 format. The .xml file contains a sequence listing entitled "033-PCT-SEQ-Listing.xml" created on Jun. 6, 2025, and having a size of 3,162 bytes and 4,096 bytes on disk. The sequence listing contained in this .xml file is part of the specification and is herein incorporated by reference in its entirety.

TECHNICAL FIELD

The disclosure relates to the field of biomedicine, in particular to a new unique human interferon alpha 2b, method of making such new unique human interferon alpha 2b, and/or methods of detecting the use of such new method of making thereof.

BACKGROUND

Interferon (IFN) was originally described more than 40 years ago as a substance that is produced upon stimulation of cells by viruses, and that has the ability to protect cells from infection with viruses of any kind, that is to interfere with viral infections. The antiviral activity of IFN was thus found to be non-specific, a fact that led to the idea that IFN might be used therapeutically against viral infections. The revolution that antibiotics had meant for bacterial infections, it was reasoned, might be paralleled by therapeutic use of IFN in viral infections. The human version is referred to as "hIFN".

The optimism regarding the potential of IFN as an antiviral therapeutic agent has not been fulfilled and for various reasons it is not until during the last decade that IFN has been established as a potent antiviral agent in chronic viral infections. In parallel with being the object of antiviral research, however, IFN has also been studied with regard to its anti-tumor properties, and it is today becoming a standard treatment in certain malignant diseases.

Although IFN was initially thought to be a single entity, later research has shown that there are multiple molecular species of IFN. Thus, there are three main classes of human IFN:s called alpha, beta and gamma interferons (IFN-alpha, IFN-beta and IFN-gamma) and a minor class called omega-IFN (IFN-Q). There are 13 genes, two of which are identical, for IFN-alpha, of which there are thus 12 subtypes, but only one gene, and no subtypes for each of IFN-beta and IFNg. IFN-alpha subtypes consist of 165 or 166, IFN-beta of 165 and IFN-gamma of 142 amino acid residues. IFN-alpha and IFN-beta were formerly called type I interferons and IFN-gamma type II or immune IFN.

The reason why there are so many subtypes of IFN-alpha remains enigmatic. However, the various subtypes of IFN-alpha vary markedly regarding their biological activities. Thus, for instance, the most pronounced antiviral activity on a molar basis is found in IFN-alpha-8, and IFN-alpha-1 has certain immunological activities that are absent among other subtypes. It therefore seems plausible that the different IFN-alpha subtypes are indeed separate cytokines which share some activities, notably the antiviral capacity, but otherwise have different functional profiles.

The present disclosure discloses anew method of making a modified hIFN-alpha 2b having proline attached to the initial cysteine at the N-terminus. In addition, such hIFN-alpha 2b can be further substituted with other amino acid in certain position(s), and/or how to detect whether such method of making was employed.

SUMMARY

In an aspect, the present disclosure relates to a composition comprising substituted Pro-hIFN alpha 2b, Pro-hIFN A2b, and/or mixture thereof. In addition, the composition can include one or more substitutions from Nle substitution at position 17, Nle substitution at position 22, Ne substitution at position 60, Nle substitution at position 112, Nle substitution at position 149, Asp substitution at position 45, and/or Lys substitution at position 66. Further the substitution can include 2 or more, 3 or more, or 4 or more substitutions.

In an aspect, the composition can include one or more substitutions from Nle substitution at position 60, Nle substitution at position 112, optionally including additional amino acid substitution Gly 45 to Asp (ASP45) and/or Asn 66 to Lys (Lys66) of Pro-hIFN A2b.

In an aspect, the composition can include one or more substitutions from Nle substitution at position 17, Nle substitution at position 22, and/or Nle substitution at position 149 of Pro-hIFN A2b.

In an aspect, the composition can include one or more substitutions from Nle substitution at position 17, Nle substitution at position 22, Nle substitution at position 60, Nle substitution at position 112, Nle substitution at position 149, amino acid substitution Gly 45 to Asp and/or Asn 66 to Lys of Pro-hIFN A2b.

In another aspect, the composition can include one or more substitutions from Nle substitution at position 17, Nle substitution at position 22, Nle substitution at position 60, Nle substitution at position 112, Nle substitution at position 149, Asp substitution at position 45, and/or Lys substitution at position 66. Alternatively, or additionally, the composition can include amino acid substation of Gly 45 to Asp and/or Asn 66 to Lys of Pro-hIFN A2b.

In another aspect, the composition can include wherein the quantitative ratio between Nle Met 60 and Met 112 to be about 1:1, 1:2, 1:3, 1:4, 1:5, 2:1, 3:1, 4:1, 5:1 or any combinations/variation thereof. Further, the quantitative ratio between Asp substitution at position 45 and Lys substitution at position 66 can include about 1:1, 1:2, 1:3, 1:4, 2:1, 3:1, 4:1, 5:1, 1:5 or any variations thereof. In an aspect, the composition can include the quantitative ratio between Nle substitution at position 17 and Nle substitution at position 22 to be about 1:1.9, 1:1.77, 1:1.87, 1:2, 1:2.5, and/or any combinations or variations thereof.

In another aspect, the composition can include the quantitative ratio between Nle Met 17, Nle Met 22, and Nle Met 149 to be about 1:0.5:1.68, 1.76:1:3.27, 0.55:0.30:1, and/or any combinations/variation thereof. Further, the quantitative ratio between Asp substitution at position 45 and Lys substitution at position 66 can include about 1:1, 1:2, 1:3, 1:4, 2:1, 3:1, 4:1, 5:1, 1:5, and/or any variations thereof.

In an aspect, the composition can include the quantitative ratio between Nle Met 60, Ne Met 112, Nle Met 17, Nle Met 22, and Nle Met 149 to be about 1:30:11:5.7:18.8, 9.58:1:3.28:1.86:6.08, 5.2:4.96:1.87:1:3.37, and/or any combinations/variation thereof. Further, the quantitative ratio between Asp substitution at position 45 and Lys substitution at position 66 can include about 1:1, 1:2, 1:3, 1:4, 2:1, 3:1, 4:1, 5:1, 1:5 or any variations thereof.

Yet in another aspect, the present disclosure relates to a pharmaceutical formulation comprising the composition according to any of the above combinations or variations and quantities, and a pharmaceutically acceptable carrier.

In an aspect, the present disclose can utilize any variations of the compositions and/or their quantity to use as a method for treating a subject in need who has a disorder including myelofibrosis, polycythemia vera, essential thrombocythaemia, and/or chronic myeloid leukemia comprising administrating to the subject a therapeutically effective amount of the composition Yet in an aspect, the myelofibrosis includes idiopathic, primary, and/or early myelofibrosis; the polycythemia vera includes high and/or low risk polycythemia vera.

Further in another aspect, any of the compound or quantity thereof above can be administered to the subject as an injection, for example, subcutaneous administration.

In an aspect, the present disclosure relates to a method for producing any of the compositions and/or its quantities mentioned above, where the method includes cloning a vector using DNA encoding the amino acid sequence of Pro-hIFN alpha 2b; transfecting said vector into a host cell; fermenting said host cell at a condition including at between about 36-37° C. with dissolved oxygen at about 40%, between about 40-45%, and/or above 45%; inducing Pro-hIFN alpha 2b expression with IPTG at a concentration of between about 0.5-0.9 mM; removing the initial methionine from said Pro-hIFN alpha 2b; refolding said Pro-hIFN alpha 2b; performing ultrafiltration on said Pro-hIFN protein; performing ammonium acetate precipitation on said Pro-hIFN alpha 2b; and purifying said Pro-hIFN alpha 2b.

In another aspect, additionally, or alternatively, some of the fermentation parameters to make Pro-hIFN alpha 2b can be adjusted to improve yield, as disclosed in United States Patent Application number US20250101484A1 (the contents of which are incorporated herein by reference in its entirety). For example, part of the fermentation can be performed including the steps of: carrying out seeding (time $S_0$) of a culture of prokaryote host cell engineered to inducibly express a recombinant protein and transferring the culture into one or more fermenters each containing a culture medium; measuring a dissolved oxygen (DO) level, an agitation rate, and a pH in the one or more fermenters; supplying a carbon source feeding solution to any of the one or more fermenters individually, whenever condition(s) (i) and/or (ii) are met: (i) said DO level exceeds above about 35% to 45% and said agitation rate exceeds about 300 to 1,000 rpm; (ii) said agitation rate exceeds about 400 to 700 rpm and said pH exceeds about 7.0 to 7.4; and supplying a nitrogen source to any of the one or more fermenters in which induction of expression of the recombinant protein has been initiated, individually, at about $I_0$ (time at initiation of induction) or $I_1$ or both; optionally, supplying a nitrogen source to any of the one or more fermenters, individually, at one or more time points selected from about $S_5$, $S_6$, $S_7$, $S_8$, $S_9$ and $S_{10}$. In an embodiment, said DO level exceeds above about 35% to 40% and said agitation rate exceeds about 300 to 700 rpm. In another aspect, said agitation rate exceeds about 500 to 600 rpm and said pH exceeds about 7.0 to 7.4. Yet in another aspect, the nitrogen source is supplied, individually, at about $I_0$ or $I_1$ or both, and at one or more time points selected from about $S_5$, $S_6$, $S_7$, $S_8$, $S_9$ and $S_{10}$. In an embodiment, a carbon source feeding solution is supplied at least once to at least one fermenter during the recombinant protein fermentation, wherein the carbon source feeding solution is a glucose feeding solution, fructose feeding solution, galactose feeding solution, pyruvate feeding solution, or any combination thereof. In another aspect, a cumulative total of about 800 to 1500 g of glucose is supplied to at least one fermenter, per about 5 L fermenter capacity, by the end of the recombinant protein fermentation. Yet in another aspect, the nitrogen source supplied to the one or more fermenters, individually, comprises potassium. In another aspect, the nitrogen source supplied to the one or more fermenters, individually, comprises a yeast extract, peptone, soytone, urea, tryptone, or any combinations thereof. Yet in an embodiment, about 40 to 150 mL of a yeast extract solution is supplied the one or more fermenters each time, individually; optionally about 300 to 1500 mL of a yeast extract solution is supplied to the one or more fermenters each time, individually. In another aspect, wherein the recombinant protein fermentation is performed with an inoculum ratio of about 6.0 to 8.5%. In an embodiment, said prokaryote host cell comprises an *E. coli* BL21, BLR-Codon Plus (DE3) cell. In another aspect, the fermentation process further comprises a step of collecting the culture of prokaryote host cell or a sample of the culture in the one or more fermenters after induction of expression of the recombinant protein, individually. In another aspect, the fermentation process further comprising processing inclusion bodies in the collected culture of prokaryote cell or sample to obtain a crude protein extract. Yet in another aspect, the culture or sample are collected after or at about $I_4$ to $I_8$. In an aspect, the fermentation processes the expressed recombinant protein in the crude protein extract, wherein the yield is about 5 to 10 μg of the recombinant protein in a fermenter having about a 5 L capacity; optionally, wherein the yield is about 20 to 30 μg of the recombinant protein in a fermenter having about a 40 L capacity.

In an aspect, the method can further include the step of detecting any number of the Nle substituted Pro-hIFN alpha 2b at any positions in the present disclosure, and/or Gly 45 to Asp, Asn 66 to Lys substitutions, or any combination thereof, or the step of quantifying said Nle-substituted, or amino acid substituted Pro-hIFN A2b.

In one aspect, the host cell includes BLR-(DE 3) with or without RIL vector.

In another aspect, the present disclosure includes a method of detecting whether a manufacturing procedure is used to produce Pro-hIFN alpha 2b, said method includes analyzing and/or quantifying the present of Nle-substituted, amino acid substituted Pro-hIFN A2b, and/or mixture thereof in a product, or any intermediate from a manufacturing procedure. In another aspect, the methods mentioned includes substitution of amino acid from Methionine to Nle at position 17, 22, 60, 112, and/or 149; and/or amino acid substitution from Gly at position 45 to Asp, Asn substitution at position 66 to Lys, and/or any combination thereof.

In another aspect, the present disclosure includes a method of detecting whether a manufacturing procedure is used to produce Pro-hIFN alpha 2b, said method includes analyzing and/or quantifying the present of Nle-substituted, amino acid substituted Pro-hIFN A2b, and/or mixture thereof in a product, or any intermediate from a manufacturing procedure. In another aspect, the methods mentioned include substitution of amino acid from Methionine to Nle at position 17, 22, and/or 149, and/or any combination thereof.

Yet in another aspect, the method according the immediate above, wherein the presence of Nle-substituted, amino acid substituted Pro-hIFN A2b, and/or mixture thereof is analyzed and/or quantified in one or more samples obtained before, during, and/or after one or more steps in a manufacturing procedure. In a further aspect, the presence of Nle-substituted, amino acid substituted Pro-hIFN A2b, and/or mixture thereof is analyzed and/or quantified in said products and/or said intermediates from one, two, or more individual batches at the end of a manufacturing procedure according to the present disclosure and/or the above.

In another aspect, the presence of any Nle-substituted, amino acid substituted Pro-hIFN A2b, and/or mixture thereof, and/or in any quantity thereof indicates one or more steps of the manufacturing process denoted in the present disclosure was used.

In yet another aspect, the method includes wherein the presence of Nle-substituted, amino acid substituted Pro-hIFN A2b, and/or mixture thereof in at least one or more batches indicates the manufacturing procedure including before and of the method disclosed herein is used to produce Pro-hIFN alpha 2b.

In an aspect, the present discuss composition comprising Pro-hIFN alpha 2b, Pro-hIFN A2b, and/or mixture thereof may be obtained by a process including mixing an *E. coli* culture supernatant containing denatured Pro-hIFN alpha 2b and/or denatured Nle substituted Pro-hIFN alpha 2b and a refolding buffer, and wherein the *E. coli* culture supernatant is produced by a procedure including fermenting a culture of *E. coli* engineered to express Pro-hIFN alpha 2b at a condition including at between about 35-37° C., with dissolved oxygen at about 40%, between about 40-45%. and/or above 45%; and optionally, the *E. coli* is BLR-(DE 3) with or without RIL vector.

Further in an aspect, the disclosure further elaborated that disclosed method above wherein the process of obtaining the composition further includes one or more filtration steps, ammonium acetate precipitation, and/or anion exchange chromatography, and the pH of the composition or method of obtaining the composition is to be maintained at between about 5.5-7.5 or below. For example, at about pH 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, or 5.5.

In one aspect, use of the composition according to the above and/or quantities for the preparation of a medicament for the treatment of one or more conditions including a subject having a disorder including myelofibrosis, polycythemia vera, essential thrombocythaemia, and/or chronic myeloid leukemia, where said myelofibrosis comprises idiopathic, primary, and/or early myelofibrosis, and the polycythemia vera comprises high and/or low risk polycythemia vera.

Yet in an aspect, the composition according to any of the present disclosure and its quantities, characterized in that it is used to treating one or more of condition including a subject having a disorder including myelofibrosis, polycythemia vera, essential thrombocythaemia, and/or chronic myeloid leukemia, where said myelofibrosis is idiopathic, primary, and/or early myelofibrosis, and/or wherein said polycythemia vera is high and/or low risk polycythemia vera.

In an aspect, not all of the Nle substituted and/or other amino acid substitution species are present in a single run.

In another aspect, no Nle substituted and/or other amino acid substitution species are produced.

BRIEF DESCRIPTION OF FIGURES

For a more complete understanding of the features and advantages of the present disclosure, reference is now made to the detailed description of the disclosure along with the accompanying figures and in which:

FIG. 1 denotes the amino acid sequence of the hIFN alpha 2b molecule, having 165 amino acids designated as SEQ ID NO:1.

FIG. 2 denotes the amino acid sequence of the modified hIFN alpha 2b molecule, having 166 amino acids designated as SEQ ID NO:2.

DETAIL DESCRIPTIONS

Figure 3:
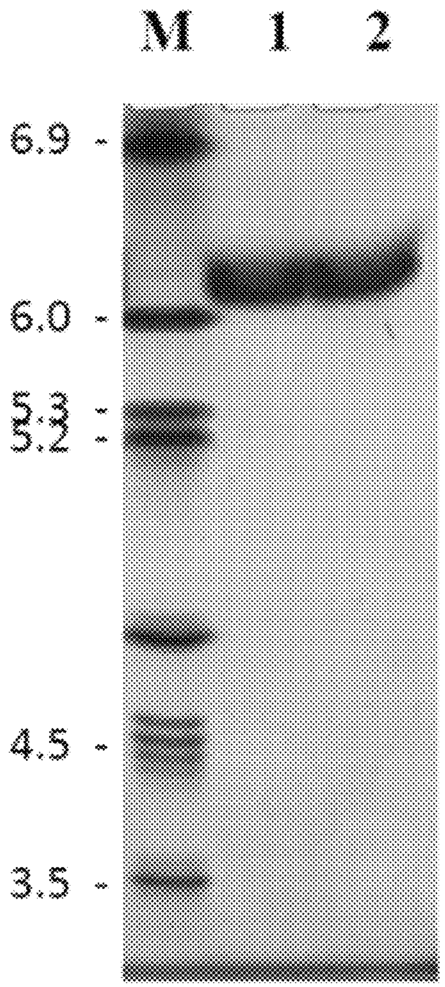
FIG. 3 denotes SDS gel electrophoresis of hIFN alpha 2b.

While the making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the disclosure and do not delimit the scope of the disclosure.

To facilitate the understanding of this disclosure, a number of terms are defined below. Terms defined herein have meanings as commonly understood by a person of ordinary skill in the areas relevant to the present disclosure. Terms such as "a", "an" and "the" are not intended to refer to only a singular entity but include the general class of which a specific example may be used for illustration. The terminology herein is used to describe specific embodiments of the disclosure, but their usage does not delimit the disclosure, except as outlined in the claims.

The following terms, unless otherwise indicated, shall be understood to have the following meanings.

As used herein, "administering," means oral administration, administration as a suppository, topical contact, intravenous, intraperitoneal, intramuscular, intralesional, intranasal or subcutaneous administration, or the implantation of a slow-release device e.g., a mini-osmotic pump, to the subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

As used herein, the term "isolated molecule" as referring to a molecule (where the molecule is, for example, a polypeptide, a polynucleotide, or an antibody) that by virtue of its origin or source of derivation (1) is not associated with naturally associated components that accompany it in its native state, (2) is substantially free of other molecules from the same source, e.g., species, cell from which it is expressed, library, etc., (3) is expressed by a cell from a different species, or (4) does not occur in nature. Thus, a molecule that is chemically synthesized, or expressed in a cellular system different from the system from which it naturally originates, will be "isolated" from its naturally associated components. A molecule also can be rendered substantially free of naturally associated components by isolation, using purification techniques well known in the art. Molecule purity or homogeneity may be assayed by a number of methods known in the art. For example, the purity of a polypeptide sample may be assayed using polyacrylamide gel electrophoresis and staining of the gel to visualize the polypeptide using techniques known in the art. For certain purposes, higher resolution may be provided by using HPLC or other means known in the art for purification.

As used herein, the terms "treating" or "treatment" or "to treat" or "alleviating" or "to alleviate" all refer to (1) therapeutic measures that cure, slow down, lessen symptoms of, and/or halt progression of a diagnosed pathologic condition or disorder and/or (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" according to the methods and molecules of the present disclosure if the patient shows, e.g., total, partial, or transient remission of a certain type of disorder.

As used herein, the term "substantially homogenous" means that the component can be at least about 90%, at least about 91%, at least about 92%, at least about 93%, at least about 94%, at least about 95%, at least about 96%, at least about 97%, at least about 98%, at least about 99%, and/or at least about 99.5%, or higher of the final preparation or more.

The terms "polypeptide", "peptide" and "protein" are used interchangeably herein to refer to chains of amino acids of any length and the chain may be linear or branched. It is understood that the polypeptides can occur as single chains or associated chains.

The term "subject" refers to a living organism that is administered with a molecule of the present disclosure and includes both humans and animals.

The term "subject in need" and "patient" are used interchangeably and refer to a living organism suffering from or prone to a condition that can be prevented or treated by administration of a molecule of the present disclosure and includes both humans and animals.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this disclosure. One example is *E. coli*. In an embodiment, the *E. coli* can be BL21 (DE3) or BLR-(DE3) with or without RIL vector which is known in the art.

As used herein, any concentration range, percentage range, ratio range or integer range is to be understood to include the value of any integer as indicated per se, as well as within the recited range and, when appropriate, fractions thereof (such as one tenth and one hundredth of an integer), unless otherwise indicated.

As used herein, an "effective dosage", "effective therapeutic amount", or "effective amount" of drug, compound, or composition is an amount sufficient to affect any one or more beneficial or desired results. In more specific aspects, an effective amount prevents, alleviates, ameliorates symptoms of disease, and/or prolongs the survival of the subject being treated. For prophylactic use, beneficial or desired results include, but not limited to eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include, but not limited to clinical results such as reducing one or more symptoms of a disease such as cancer. An effective dosage can be administered in one or more administrations. For purposes of this disclosure, an effective dosage of drug, compound, or composition is an amount sufficient to accomplish prophylactic or therapeutic treatment either directly or indirectly. As is understood in the clinical context, an effective dosage of a drug, compound, or composition may or may not be achieved in conjunction with another drug, compound, or pharmaceutical composition. Thus, an "effective dosage" or "effective amount" may be considered in the context of administering one or more therapeutic agents, and a single agent may be considered to be given in an effective amount if, in conjunction with one or more other agents, a desirable result may be or is achieved.

As used herein, the term "hIFN alpha 2b" or "hIFN-A2b" refer to the human version of interferon having category alpha in class 2b, wherein the amino acid sequence is in FIG. 1 (SEQ ID NO:1).

As used herein, the term "Pro-hIFN" or "Pro-hIFN-A2b" refer to modified hIFN alpha 2b having the amino acid sequence denoted in FIG. 2 (SEQ ID NO:2).

As used herein, the term "Norleucine" or "Ne" is an amino acid with the formula $CH_3(CH_2)_3CH(NH_2)CO_2H$. A systematic name for this compound is 2-aminohexanoic acid.

As used herein, the term "Nle substituted Pro-hIFN" or "Nle incorporated Pro-hIFN-A2b" refers to modified hIFN alpha 2b having one or more amino acid sequence Nle substitution and/or other substitution in one or more position of the sequence denoted in SEQ ID NO:2.

As used herein, the term "other amino acid substituted Pro-IFN alfa-2b" or "amino acid substituted Pro-IFN alfa-2b" refer to modified hIFN alpha 2b having one or more amino acid sequence substitution in one or more position of the sequence denoted in SEQ ID NO:2. For example, Asp substitution at position 45 for Gly and Lys substitution at position 66 for Asn of the sequence denoted in SEQ ID NO:2.

As used herein, the term "per dose", "dosage", or "dose" means administering a given numeric amount of drug to a subject. Per dose can be administered in separate injections at about the same time and/or different time, so long as a subject receives the drug amount.

As used herein, the term "per injection" means administering the entire numeric amount of drug to a subject for a given dose in a single injection.

As used herein, "substantially" or "substantially all" means more than about 50%, 60%, 70%, 80%, 90%, 92.5%, 95%, 97.5%, 98%, 99%, 99.5%, 99.95% or 100% of a molecule.

As used herein, "vector" or "expression vector" means a construct, which is capable of delivering, and expressing one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "pharmaceutically acceptable carrier" or "pharmaceutical acceptable excipient" includes any material which, when combined with an active ingredient, allows the ingredient to retain biological activity or stability and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by known methods.

The term "intradermal administration", "i.d.", or "administered intradermally," in the context of administering a substance to a mammal including a human, refers to the delivery of the substance into the dermis layer of the skin of the mammal. The skin of a mammal is composed of an epidermis layer, a dermis layer, and a subcutaneous layer. The epidermis is the outer layer of the skin. The dermis, which is the middle layer of the skin, contains nerve endings, sweat glands and oil (sebaceous) glands, hair follicles, and blood vessels. The subcutaneous layer is made up of fat and connective tissue that houses larger blood vessels and nerves. In contrast in intradermal administration, "s.c.", or "subcutaneous administration", refers to the administration of a substance into the subcutaneous layer and "topical administration" refers to the administration of a substance onto the surface of the skin.

As used herein, "about" means within an acceptable error range for the particular value as determined by one of ordinary skill in the art, which will depend in part on how the value is measured or determined, i.e., the limitations of the measurement system. For example, "about" can mean within 1 or more than 1 standard deviation per the practice in the art. Alternatively, "about" can mean a range of up to 5%, 7.5%, 10%, 12.5%, 15%, 17.55, 20%, 22.5% 25%, 27.5%, 30%, 32.5%, 35%, 37.5%, or 40% of difference in either direction (positive or negative) compared to a reference value. Furthermore, particularly with respect to biological systems or processes, the terms can mean up to an order of magnitude or up to 1, 2, 3, 4, or 5-folds of a value. When particular values are provided in the application and claims, unless otherwise stated, the meaning of "about" should be assumed to be within an acceptable error range for that particular value. Reference to "about" a value or parameter herein includes (and describes) embodiments that are directed to that value or parameter per se. For example, description referring to "about X" includes description of "X". Numeric ranges are inclusive of the numbers defining the range.

Peptide/Nucleotide Sequence of hIFN Alpha 2b and Pro-hIFN

In an embodiment, the present disclosure includes a biologics molecule having 165 amino acids, and one particular example is denoted in FIG. 1 as SEQ ID No.:1. The biologics molecule is known as IFN alfa-2b.

In another embodiment, the present disclosure includes a biologics molecule having 166 amino acids Pro-IFN alfa-2b as shown in FIG. 2. In particular, it is bacterially produced with extra N-terminal Methionine (Met) and Proline (Pro) and the Met is removed via method known in the art.

Yet in an embodiment, one or more amino acid of Pro-IFN alfa-2b can have amino acid Nle substituted and/or other amino acid substituted. Yet in another embodiment, the present composition can contain Pro-IFN alfa-2b, Nle substituted and/or other amino acid substituted Pro-IFN alfa-2b, and/or mixture thereof. For example, the one or more amino acid substituted Pro-hIFN alpha 2b comprises Nle60 and Asp45 in SEQ ID NO:2; the one or more amino acid substituted Pro-hIFN alpha 2b comprises Nle17 and Nle112 in SEQ ID NO:2; the one or more amino acid substituted Pro-hIFN alpha 2b comprises Nle17 and Nle149 in SEQ ID NO:2; the one or more amino acid substituted Pro-hIFN alpha 2b comprises Nle17 and Nle22 in SEQ ID NO:2; the one or more amino acid substituted Pro-hIFN alpha 2b comprises Nle149 and Asp45 in SEQ ID NO:2; the one or more amino acid substituted Pro-hIFN alpha 2b comprises Nle149 and Lys66 in SEQ ID NO:2; the one or more amino acid substituted Pro-hIFN alpha 2b comprises Nle17 and Lys66 in SEQ ID NO:2; the one or more amino acid substituted Pro-hIFN alpha 2b comprises Nle60 and Lys66 in SEQ ID NO:2; the one or more amino acid substituted Pro-hIFN alpha 2b comprises Nle60, Asp45 and Lys66 in SEQ ID NO:2; the one or more amino acid substituted Pro-hIFN alpha 2b comprises Nle112 and Asp45 in SEQ ID NO:2; the one or more amino acid substituted Pro-hIFN alpha 2b comprises Nle112 and Lys66 in SEQ ID NO:2; the one or more amino acid substituted Pro-hIFN alpha 2b comprises Nle112, Asp45 and Lys66 in SEQ ID NO:2; the one or more amino acid substituted Pro-hIFN alpha 2b comprises Nle60, Nle112 and Asp45 in SEQ ID NO:2; the one or more amino acid substituted Pro-hIFN alpha 2b comprises Nle60, Nle112 and Lys66 in SEQ ID NO:2; the one or more amino acid substituted Pro-hIFN alpha 2b comprises Nle60, Nle112, Asp45 and Lys66 in SEQ ID NO:2; and/or the one or more amino acid substituted Pro-hIFN A2b comprises Asp45 and Lys 66. In an embodiment, the presence of any Nle-substituted, amino acid substituted Pro-hIFN A2b, and/or mixture thereof, and/or in any quantity thereof indicates one or more steps of the manufacturing process denoted in the present disclosure was used.

In another embodiment, alternatively, or additionally, the Nle substituted Pro-hIFN A2b can include Ne substitution at one or more positions selected from Nle17, Nle22 and Nle149 of SEQ ID No:2. In another embodiment, the Nle substituted Pro-hIFN A2b can include Nle substitution at one or more positions selected from Nle17, Nle22, Nle60, Nle112, and/or Nle149. Alternatively or additionally, the Nle substituted Pro-hIFN A2b can include Nle substitution at one or more positions selected from Nle17, Nle22, Nle60, Nle112, Nle149, and amino acid substitution at Asp 45 with Gly, and/or with or without substitution at Lys66 with Asn, or any combination thereof.

The nucleotide sequences encoding such amino acid can vary such as using codon optimization, if needed, and depending on which host cell is used. Such method is known in the art. The nucleotide sequence can be cloned into a vector and transfect into a bacterial host cell for protein expression by methods known in the art.

In another embodiment, the detection and/or qualification for Nle substituted or other amino acid substituted sequence can be utilized at his very stage. These samples can be collected and further analyzed by RP-HPLC and peptide mapping. In an embodiment, peptide mapping analysis can identify and quantify one or more amino acid substituted Pro-hIFN alpha 2b comprises Nle60 and Asp45 in SEQ ID NO:2; the one or more amino acid substituted Pro-hIFN alpha 2b comprises Nle60 and Lys66 in SEQ ID NO:2; the one or more amino acid substituted Pro-hIFN alpha 2b comprises Nle17 and Nle112 in SEQ ID NO:2; the one or more amino acid substituted Pro-hIFN alpha 2b comprises Nle22 and Nle149 in SEQ ID NO:2; the one or more amino acid substituted Pro-hIFN alpha 2b comprises Nle17 and Nle22 in SEQ ID NO:2; the one or more amino acid substituted Pro-hIFN alpha 2b comprises Nle149 and Asp45 in SEQ ID NO:2; the one or more amino acid substituted Pro-hIFN alpha 2b comprises Nle149 and Lys66 in SEQ ID NO:2; the one or more amino acid substituted Pro-hIFN alpha 2b comprises Nle17 and Lys66 in SEQ ID NO:2; the one or more amino acid substituted Pro-hIFN alpha 2b comprises Nle60, Asp45 and Lys66 in SEQ ID NO:2; the one or more amino acid substituted Pro-hIFN alpha 2b comprises Nle112 and Asp45 in SEQ ID NO:2; the one or more amino acid substituted Pro-hIFN alpha 2b comprises Nle112 and Lys66 in SEQ ID NO:2; the one or more amino acid substituted Pro-hIFN alpha 2b comprises Nle112, Asp45 and Lys66 in SEQ ID NO:2; the one or more amino acid substituted Pro-hIFN alpha 2b comprises Nle60, Nle112 and Asp45 in SEQ ID NO:2; the one or more amino acid substituted Pro-hIFN alpha 2b comprises Nle60, Nle112 and Lys66 in SEQ ID NO:2; the one or more amino acid substituted Pro-hIFN alpha 2b comprises Nle60, Nle112, Asp45 and Lys66 in SEQ ID NO:2; and/or the one or more amino acid substituted Pro-hIFN A2b comprises Asp45 and Lys 66.

In another embodiment, the detection and/or qualification for Nle substituted or other amino acid substituted sequence can be utilized at various stage of manufacturing. These samples can be collected and further analyzed by RP-HPLC and peptide mapping. In an embodiment, peptide mapping analysis can identify and quantify one or more amino acid substituted Pro-hIFN alpha 2b comprises Nle60 and Asp45 in SEQ ID NO:2; the one or more amino acid substituted Pro-hIFN alpha 2b comprises Nle60 and Lys66 in SEQ ID NO:2; the one or more amino acid substituted Pro-hIFN alpha 2b comprises Nle17 and Nle112 in SEQ ID NO:2; the one or more amino acid substituted Pro-hIFN alpha 2b comprises Nle22 and Nle149 in SEQ ID NO:2; the one or more amino acid substituted Pro-hIFN alpha 2b comprises Nle17 and Nle22 in SEQ ID NO:2; the one or more amino acid substituted Pro-hIFN alpha 2b comprises Nle149 and Gly substitution to Asp45 in SEQ ID NO:2; the one or more amino acid substituted Pro-hIFN alpha 2b comprises Nle149 and Asn to Lys66 in SEQ ID NO:2; the one or more amino acid substituted Pro-hIFN alpha 2b comprises Nle17 and Asn to Lys66 substitution in SEQ ID NO:2; the one or more amino acid substituted Pro-hIFN alpha 2b comprises Nle60, Gly substitution to Asp45 and Lys66 in SEQ ID NO:2; the one or more amino acid substituted Pro-hIFN alpha 2b comprises Nle112 and Gly substitution to Asp45 in SEQ ID NO:2; the one or more amino acid substituted Pro-hIFN alpha 2b comprises Nle112 and Asn substitution to Lys66 in SEQ ID NO:2; the one or more amino acid substituted Pro-hIFN alpha 2b comprises Nle112, Gly substitution to Asp45 and Asn substitution to Lys66 in SEQ ID NO:2; the one or more amino acid substituted Pro-hIFN alpha 2b comprises Nle60, Nle112 and Asp45 in SEQ ID NO:2; the one or more amino acid substituted Pro-hIFN alpha 2b comprises Nle60, Nle112 and Asn substitution to Lys66 in SEQ ID NO:2; the one or more amino acid substituted Pro-hIFN alpha 2b comprises Nle60, Nle112, Gly substitution to Asp45 and Asn substitution to Lys66 in SEQ ID NO:2; and/or the one or more amino acid substituted Pro-hIFN A2b comprises Gly substitution to Asp45 and Asn substitution to Lys 66. Additionally, or alternatively, the mere fact that the detection of existence of Nle at position 17, Nle at position 22, Nle at position 60, Nle at position Met 112, Nle at position 149 or substitution at Gly substitution to Asp45/Asn substitution to Lsy66 of Pro-hIFN alpha 2b in any amount and/or quantitative ratio indicates the manufacturing method of the present disclosure was used. In another embodiment, the detection ratio before or after any manufacturing step(s) of the present disclosure between the amount of Gly 45 to Asp, and Asn 66 to Lys may be about 1:1, 1:2, 1:3, 1:4, 1:5, 2:1, 3:1, 4:1, 5:1, or any variation thereof, indicates any part, or the whole manufacturing method of the present disclosure was utilized.

Yet in another embodiment, the mere fact that the detection of existence of Nle at Met 60, Met 112 before or after any manufacturing step(s) of the present disclosure at the ratio of about 1:1, 1:2, 1:3, 2:1, 3:1, or any variations thereof also indicates any part, or the whole manufacturing method of the present disclosure was utilized.

In another embodiment, the composition can include the quantitative ratio between Nle at Met 17, Nle at Met 22, and Nle at Met 149 to be about 1:0.5:1.68, 1.76:1:3.27, 0.55:0.30:1, and/or any combinations/variation thereof. Further, the quantitative ratio between Asp substitution at position 45 and Lys substitution at position 66 can include about 1:1, 1:2, 1:3, 1:4, 2:1, 3:1, 4:1, 5:1, 1:5, and/or any variations thereof. In another embodiment, the detection of the present or any ratio thereof, indicates any part, or the whole manufacturing method of the present disclosure.

In an embodiment, the composition can include the quantitative ratio between Nle at Met 60, Nle at Met 112, Nle at Met 17, Nle at Met 22, and at Nle Met 149 to be about 1:30:11:5.7:18.8, 9.58:1:3.28:1.86:6.08, 5.2:4.96:1.87:1:3.37, and/or any combinations/variation thereof. Further, the quantitative ratio between Asp substitution at position 45 and Lys substitution at position 66 can include about 1:1, 1:2, 1:3, 1:4, 2:1, 3:1, 4:1, 5:1, 1:5 or any variations thereof. In another embodiment, the detection of the present or any ratio thereof, indicates any part, or the whole manufacturing method of the present disclosure.

Detection method of either Nle at position 17, Nle at position 22, Nle at position 60, Nle at position Met 112, and/or Nle at position 149, and/or amino acid substitution at Gly substitution to Asp45/Asn substitution to Lsy66 of Pro-hIFN alpha 2b in any amount and/or quantitative ratio is known in the art. Nonlimiting example include running trypsin digestion peptide mapping, various types of HPLC, and/or various types of mass spectroscopy, such as LC-MS.

ii. Method of Making

Previously, a method to generate Pro-IFN A2b is known. See U.S. Pat. No. 8,106,160, the content of which are incorporated herein by reference in their entirety. In U.S. Pat. No. 8,106,160, no Nle substituted and/or other amino acid substituted Pro-IFN A2b was reported. Here, in an embodiment, the method of making is not identical, and amino acid substituted and/or Nle substituted or other amino acid substitution Pro-hIFN alpha 2b can be produced, but not necessarily all the time. In an embodiment, the presence of substituted and/or Ne substituted or other amino acid substitution Pro-hIFN alpha 2b can be detected at a frequency 90%, 91%, 92%, 93%, 94%, 95%, 96%, 97%, 98%, 99%, 99.5%, 99.9% and/or 99.99% over time.

In an embodiment, the present disclosure provides new methods of generating and making Nle substituted, amino acid substituted Pro-hIFN A2b, Pro-hIFN A2b, and/or mixture thereof.

Briefly, and in general, DNA encoding amino acid of SEQ ID No:2 with is constructed in a vector, and such vectors encoding Pro-hIFN are transfected to host cells such as *E. coli*. Then, the host cells are first inoculated, and cultured in a fermentor. Induction is conducted with IPTG (Isopropyl β-D-1-thiogalactopyranoside) to induce protein product in the host cell, and then the cells are harvested. Optionally, in one embodiment and alternatively or additionally, post IPTG, an amount of about 1.0, 2.0, 3.0, 4.0, 5.0, 6.0, 7.0, 8.0, 9.0, 10.0 mM or higher norleucine solution in formic can be added. The cell pellet is then stored. Then, the cell pellet is homogenized to obtain a crude lysate which contains the protein Pro-hIFN. The initial methionine, which is added on by *E. coli*, is then removed, and crude lysate protein is then refolded by method known in the art, and clarified to obtain crude refolded protein solution. The crude solution is then concentrated and subjected to filtration, chromatography, and/or hydrophobic interaction chromatography to obtain Nle-incorporated and/or other amino acid substituted Pro-hIFN A2b, Pro-hIFN A2b, and/or mixture thereof.

In another embodiment, additionally, or alternatively, some of the fermentation parameters can be adjusted to improve yield, as disclosed in United States Patent Application number US20250101484A1. The contents of which are incorporated herein by reference in its entirety. For example, part of the fermentation can be performed including the steps of: carrying out seeding (time S0) of a culture of prokaryote host cell engineered to inducibly express a recombinant protein and transferring the culture into one or more fermenters each containing a culture medium; measuring a dissolved oxygen (DO) level, an agitation rate, and a pH in the one or more fermenters; supplying a carbon source feeding solution to any of the one or more fermenters individually, whenever condition(s) (i) and/or (ii) are met: (i) said DO level exceeds above about 35% to 45% and said agitation rate exceeds about 300 to 1,000 rpm; (ii) said agitation rate exceeds about 400 to 700 rpm and said pH exceeds about 7.0 to 7.4; and supplying a nitrogen source to any of the one or more fermenters in which induction of expression of the recombinant protein has been initiated, individually, at about $I_0$ (time at initiation of induction) or I1 or both; optionally, supplying a nitrogen source to any of the one or more fermenters, individually, at one or more time points selected from about S5, S6, S7, S8, S9 and S10. In an embodiment, said DO level exceeds above about 35% to 40% and said agitation rate exceeds about 300 to 700 rpm. In another embodiment, said agitation rate exceeds about 500 to 600 rpm and said pH exceeds about 7.0 to 7.4. Yet in another embodiment, the nitrogen source is supplied, individually, at about I0 or I1 or both, and at one or more time points selected from about S5, S6, S7, S8, S9 and 510. In an embodiment, a carbon source feeding solution is supplied at least once to at least one fermenter during the recombinant protein fermentation, wherein the carbon source feeding solution is a glucose feeding solution, fructose feeding solution, galactose feeding solution, pyruvate feeding solution, or any combination thereof. In another embodiment, a cumulative total of about 800 to 1500 g of glucose is supplied to at least one fermenter, per about 5 L fermenter capacity, by the end of the recombinant protein fermentation. Yet in another embodiment, the nitrogen source supplied to the one or more fermenters, individually, comprises potassium. In another embodiment, the nitrogen source supplied to the one or more fermenters, individually, comprises a yeast extract, peptone, soytone, urea, tryptone, or any combinations thereof. Yet in an embodiment, about 40 to 150 mL of a yeast extract solution is supplied the one or more fermenters each time, individually; optionally about 300 to 1500 mL of a yeast extract solution is supplied to the one or more fermenters each time, individually. In another embodiment, wherein the recombinant protein fermentation is performed with an inoculum ratio of about 6.0 to 8.5%. In an embodiment, said prokaryote host cell comprises an *E. coli* BLR-Codon Plus (DE3) cell. In another embedment, the fermentation process further comprising a step of collecting the culture of prokaryote host cell or a sample of the culture in the one or more fermenters after induction of expression of the recombinant protein, individually. In another embodiment, the fermentation process further comprising processing inclusion bodies in the collected culture of prokaryote cell or sample to obtain a crude protein extract. Yet in another embodiment, the culture or sample are collected after or at about 14 to 18. In an embodiment, the fermentation processes the expressed recombinant protein in the crude protein extract, wherein the yield is about 5 to 10 µg of the recombinant protein in a fermenter having about a 5 L capacity; optionally, wherein the yield is about 20 to 30 µg of the recombinant protein in a fermenter having about a 40 L capacity.

In an embodiment, at this stage, the mere fact that the detection of existence of Nle at Met 60, Met 112 or Asp45/Lsy66 in any ratio indicates the present disclosure's method was used. In another embodiment, the detection ratio before or after any manufacturing step(s) of the present disclosure between the amount of Gly 45 to Asp, and Asn 66 to Lys may be about 1:1, 1:2, 1:3, 1:4, 1:5, 2:1, 3:1, 4:1, 5:1, or any variation thereof, indicates present disclosure's method, in part or in whole, was utilized.

Yet in another embodiment, the mere fact that the detection of existence of Nle at Met 60, Met 112 before or after any manufacturing step(s) of the present disclosure at the ratio of about 1:1, 1:2, 1:3, 2:1, 3:1, or any variations thereof also indicates any part of the present disclosure's method, in part or in whole, was utilized.

Pharmaceutically Acceptable Carriers

The composition used in the present disclosure, whether Nle-incorporated and/or other amino acid substituted Pro-hIFN A2b, Pro-hIFN A2b, and/or mixture thereof alone, or with any combinations of other active ingredients thereof, can further comprise pharmaceutically acceptable carriers, excipients, or stabilizers, in the form of lyophilized formulations or aqueous solutions. Carriers, excipients, or stabilizers can be nontoxic to recipients at the dosages and concentrations, and can comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN (trademarked), PLURONICS (trademarked).

Dosage

In an embodiment, a subject can be treated with Nle-substituted, other amino acid substituted Pro-hIFN A2b, Pro-hIFN A2b, and/or mixture thereof for a disease. In another embodiment, a disease or indication can be myelofibrosis of any subtype (e.g., idiopathic, primary, and/or early), polycythemia vera (high or low risk), essential thrombocythaemia, and/or chronic myeloid leukemia.

Yet in an embodiment, a treatment period using Nle-substituted, other amino acid substituted Pro-hIFN A2b, Pro-hIFN A2b, and/or mixture thereof can be at least about 1, 2, 3, 4, 5, 6, 7, 8, 9, 10, 11, 12, 24, 36, 42, 48, 54, 60, 66, 72, 78, 84 or more than 84 months. In some embodiments, the treatment period is about 0.1, 0.25, 0.5, 0.75, 1, 2, 3, 4, 4.5, 5, 5.5, 6, 6.5, 7, 7.5, 8, 8.5, 9, 9.5, 10 or more than 10 years. In some embodiments, the treatment period is at least about 0.1, 0.25, 0.5, 0.75, 1, 2, 3, 4, 5, 6, 7, 8, 12, 14, 15, 16, 17, 18, 19, 20, 24, 28, 32, 36, 40, 44, 48, 52, 56, 60 weeks or longer than 60 weeks.

In another embodiment, Nle-substituted, other amino acid substituted Pro-hIFN A2b, Pro-hIFN A2b, and/or mixture thereof can be administered for treating myelofibrosis of any subtype (e.g., idiopathic, primary, and/or early), polycythemia vera (high or low risk), essential thrombocythaemia, and/or chronic myeloid leukemia using between about 50 to 540 μg per dose or per injection subcutaneously, via i.d., or other routes. Alternatively, or additionally, a dose or injection of Nle-substituted, other amino acid substituted Pro-hIFN A2b, Pro-hIFN A2b, and/or mixture thereof can be administered during the treatment period ranges from about 250 to about 650 μg. The dose/injection can also be up to about 250 μg, up to about 255 μg, up to about 260 μg, up to about 265 μg, up to about 270 μg, up to about 275 μg, up to about 280 μg, up to about 285 μg, up to about 290 μg, up to about 295 μg, up to about 300 μg, up to about 305 μg, up to about 310 μg, up to about 315 μg, up to about 320 μg, up to about 325 μg, up to about 330 μg, up to about 335 μg, up to about 340 μg, up to about 345 μg, up to about 350 μg, up to about 400 μg, up to about 450 μg, up to about 500 μg, up to about 540 μg, or up to about 650 μg. Alternatively, or additionally, a dose or injection of 135 μg or 180 μg of Nle-substituted, other amino acid substituted Pro-hIFN A2b, Pro-hIFN A2b, and/or mixture thereof can be administered.

In another embodiment, Nle-substituted, other amino acid substituted Pro-hIFN A2b, Pro-hIFN A2b, and/or mixture thereof can be administered for treating myelofibrosis of any subtype (e.g., idiopathic, primary, and/or early), polycythemia vera (high or low risk), essential thrombocythaemia, and/or chronic myeloid leukemia using between about 50 to 540 μg per dose or per injection subcutaneously, via i.d., or other routes every week. Alternatively, or additionally, a dose or injection of Nle-substituted, other amino acid substituted Pro-hIFN A2b, Pro-hIFN A2b, and/or mixture thereof can be administered during the treatment period ranges from about 250 to about 650 μg. The dose/injection can also be up to about 250 μg, up to about 255 μg, up to about 260 μg, up to about 265 μg, up to about 270 μg, up to about 275 μg, up to about 280 μg, up to about 285 μg, up to about 290 μg, up to about 295 μg, up to about 300 μg, up to about 305 μg, up to about 310 μg, up to about 315 μg, up to about 320 μg, up to about 325 μg, up to about 330 μg, up to about 335 μg, up to about 340 μg, up to about 345 μg, up to about 350 μg, up to about 400 μg, up to about 450 μg, up to about 500 μg, up to about 540 μg, or up to about 650 μg every week. Alternatively, or additionally, a dose or injection of 135 μg or 180 μg of Nle-substituted, other amino acid substituted Pro-hIFN A2b, Pro-hIFN A2b, and/or mixture thereof can be administered every week.

In another embodiment, Nle-substituted, other amino acid substituted Pro-hIFN A2b, Pro-hIFN A2b, and/or mixture thereof can be administered for treating myelofibrosis of any subtype (e.g., idiopathic, primary, and/or early), polycythemia vera (high or low risk), essential thrombocythaemia, and/or chronic myeloid leukemia using between about 50 to 540 μg per dose or per injection subcutaneously, via i.d., or other routes every 2 weeks. Alternatively, or additionally, a dose or injection of Nle-substituted, other amino acid substituted Pro-hIFN A2b, Pro-hIFN A2b, and/or mixture thereof can be administered during the treatment period ranges from about 250 to about 650 μg. The dose/injection can also be up to about 250 μg, up to about 255 μg, up to about 260 μg, up to about 265 μg, up to about 270 μg, up to about 275 μg, up to about 280 μg, up to about 285 μg, up to about 290 μg, up to about 295 μg, up to about 300 μg, up to about 305 μg, up to about 310 μg, up to about 315 μg, up to about 320 μg, up to about 325 μg, up to about 330 μg, up to about 335 μg, up to about 340 μg, up to about 345 μg, up to about 350 μg, up to about 400 μg, up to about 450 μg, up to about 500 μg, up to about 540 μg, or up to about 650 μg every 2 weeks. Alternatively, or additionally, a dose or injection of 135 μg or 180 μg of Nle-substituted, other amino acid substituted Pro-hIFN A2b, Pro-hIFN A2b, and/or mixture thereof can be administered every 2 weeks.

Yet in another embodiment, Nle-substituted, other amino acid substituted Pro-hIFN A2b, Pro-hIFN A2b, and/or mixture thereof can be administered for treating myelofibrosis of any subtype (e.g., idiopathic, primary, and/or early), polycythemia vera (high or low risk), essential thrombocythaemia, and/or chronic myeloid leukemia using between about 50 to 540 μg per dose or per injection subcutaneously, via i.d., or other routes every 3 weeks. Alternatively, or additionally, a dose or injection of Nle-substituted, other amino acid substituted Pro-hIFN A2b, Pro-hIFN A2b, and/or mixture thereof can be administered during the treatment period ranges from about 250 to about 650 μg. The dose/injection can also be up to about 250 μg, up to about 255 μg, up to about 260 μg, up to about 265 μg, up to about 270 μg, up to about 275 μg, up to about 280 μg, up to about 285 μg, up to about 290 μg, up to about 295 μg, up to about 300 μg, up to about 305 μg, up to about 310 μg, up to about 315 μg, up to about 320 μg, up to about 325 μg, up to about 330 μg, up to about 335 μg, up to about 340 μg, up to about 345 μg, up to about 350 μg, up to about 400 μg, up to about 450 μg, up to about 500 μg, up to about 540 μg, or up to about 650 μg every 3 weeks. Alternatively, or additionally, a dose or injection of 135 μg or 180 μg of Nle-substituted, other amino acid substituted Pro-hIFN A2b, Pro-hIFN A2b, and/or mixture thereof can be administered every 3 weeks.

In another embodiment, Nle-substituted, other amino acid substituted Pro-hIFN A2b, Pro-hIFN A2b, and/or mixture thereof can be administered for treating myelofibrosis of any subtype (e.g., idiopathic, primary, and/or early), polycythemia vera (high or low risk), essential thrombocythaemia, and/or chronic myeloid leukemia using between about 50 to 540 μg per dose or per injection subcutaneously, via i.d., or other routes every 4 weeks. Alternatively, or additionally, a dose or injection of Nle-substituted, other amino acid substituted Pro-hIFN A2b, Pro-hIFN A2b, and/or mixture thereof can be administered during the treatment period ranges from about 250 to about 650 μg. The dose/injection can also be up to about 250 μg, up to about 255 μg, up to about 260 μg, up to about 265 μg, up to about 270 μg, up to about 275 μg, up to about 280 μg, up to about 285 μg, up to about 290 μg, up to about 295 μg, up to about 300 μg, up to about 305 μg, up to about 310 μg, up to about 315 μg, up to about 320 μg, up to about 325 μg, up to about 330 μg, up to about 335 μg, up to about 340 μg, up to about 345 μg, up to about 350 μg, up to about 400 μg, up to about 450 μg, up to about 500 μg, up to about 540 μg, or up to about 650 μg every 4 weeks. Alternatively, or additionally, a dose or injection of 135 μg or 180 μg of Nle-substituted, other amino acid substituted Pro-hIFN A2b, Pro-hIFN A2b, and/or mixture thereof can be administered every 4 weeks.

In one embodiment, Nle-substituted, other amino acid substituted Pro-hIFN A2b, Pro-hIFN A2b, and/or mixture thereof can be administered or dosed for treating myelofibrosis of any subtype (e.g., idiopathic, primary, and/or early), polycythemia vera (high or low risk), essential thrombocythaemia, and/or chronic myeloid leukemia according to the formula 0.75-1.5 μg/kg/wk where the ag is amount of Nle-substituted, other amino acid substituted Pro-hIFN A2b, Pro-hIFN A2b, and/or mixture thereof, kg is a subject's weight and wk is week.

In some embodiments, an initial (starting) dose for treating myelofibrosis of any subtype (e.g., idiopathic, primary, and/or early), polycythemia vera (high or low risk), essential thrombocythaemia, and/or chronic myeloid leukemia can be about 250 to about 500 μg (e.g., about 250 μg, about 300 μg, about 350, about 400 μg, about 450 μg, or about 500 μg) of Nle-substituted, other amino acid substituted Pro-hIFN A2b, Pro-hIFN A2b, and/or mixture thereof administered to the subject. The initial dose/injection can be maintained or varied during the treatment period depending on patient's need and/or physician's recommendation.

In any of the methods or treatment periods and/or dosage described herein for Nle-substituted, other amino acid substituted Pro-hIFN A2b, Pro-hIFN A2b, and/or mixture thereof can be titrated. As non-limiting example, a subject can be treated for treating myelofibrosis of any subtype (e.g., idiopathic, primary, and/or early), polycythemia vera (high or low risk), essential thrombocythaemia, and/or chronic myeloid leukemia with a lower starting dose/injection (e.g., about 50 μg, about 100 μg, about 150 μg, about 200 μg, or about 250 to about 500 μg) of the Nle-substituted, other amino acid substituted Pro-hIFN A2b, Pro-hIFN A2b, and/or mixture thereof. If the subject responds well (e.g., lack of significant drug-related adverse events, significant self-reported discomfort, abnormal hematological responses, or other symptoms) after a time (e.g., between about 1 to 26 weeks, 1 to 52 weeks, or more than 52 weeks), the dose/injection given to the subject can be increased incrementally (e.g., by between about 50 to 250 μg, such as at about 50 μg, about 75 μg, about 100 μg, about 125 μg, about 150 μg, about 200 μg, about 250 μg or a combination thereof) every 2 to 16 weeks (e.g., every 1, 2, 3, 4, 5, 6, 7, 8, 9, 10, 11, 12, 13, 14, 15, or 16 weeks, or a combination thereof) until the dose reaches a target dose (e.g., at least about 400 μg, at least about 425 μg, at least about 450 μg, at least about 475 μg, at least about 500 μg, at least about 525 μg, at least about 550 μg, or at least about 650 μg). After that, a target dose can be maintained during the treatment period, increased, and/or decreased depend on subject's condition. The dose/injection can also be increased successively until the desired target dose is reached. For example, if the Nle-substituted, other amino acid substituted/Nle substituted Pro-hIFN A2b, Pro-hIFN A2b, and/or mixture thereof can be administered once every 1, 2, 3, 4, 5, 6, 7, or 8 weeks, the dose/injection can be increased every 1, 2, 3, 4, 5, 6, 7 or 8 weeks, respectively. In some embodiments, a subject can be given a starting dose/injection of 250 μg (i.e., at week 0). If the subject responds well to the initial dose/injection, the dose/injection can be increased by about 100 to about 150 μg every 2 to 8 weeks until it reaches a target dose of about 500 μg, about 550 μg, and/or 600 μg. For example, a 250-350-500 μg dosing schedule can be implemented (i.e., about 250 μg at week 0, about 350 μg between about week 2 to 8, and about 500 μg at the third administration 2 to 8 weeks after the initial second dose, without other intervening doses). Alternative or additionally, a subject can be for treating myelofibrosis of any subtype (e.g., idiopathic, primary, and/or early), polycythemia vera (high or low risk), essential thrombocythaemia, and/or chronic myeloid leukemia by given a starting dose/injection of about 350 μg and a second dose of about 500 μg between about 2 to 16 weeks thereafter without an intervening dose (i.e., 350-500). Exemplary dosing schedules can be abbreviated, nonetheless, each number is approximated. For example, 250-350-500 includes 1st dose/injection administered at about 250 μg, 2nd dose/injection administered at about 350 μg, and 3rd dose/injection administered at about 500 μg. Other embodiments include, but are not limited to: 250-400-500, 250-400, 250-500, 250-400-500, 250-450, 250-350-400-500, 250-300-400-500, 250-350-450-500, 250-350-450, 250-250-350-500, 250-250-250-350-500, 250-350-350-500, 250-500-500-500 (and remain at 500 afterwards), 350-500, 350-400-500, 350-400-450-500, 350-450-500, 350-400, 350-450, 350-350-500, 350-350-350-500, 400-450-500, 400-500, 400-400-500, 450-500 μg. In some embodiments, the target dose and/or desirable effect is reached between about 1 to 13 weeks, about 1 to 26 weeks, 1 to 52 weeks, or more than 52 weeks from the initial administration. During the titration process, any dose, prior to reaching the target dose, may be maintained for a time period (e.g., between about 4 to 16 weeks) or a number of successive doses dose/injection (e.g., between 2 to 8 successive doses dose/injection, e.g., 250-350-350-500 μg) or reduced depending on the subject's response. In some embodiments, the target dose is reached within about 2 to 8 successive doses. In further embodiments, once the subject is clinically stable, the dose/injection can be maintained at a constant level for a given treatment period, which can be at least about 1, 2, 3, 4, 5, 6, 7, 8, 12, 14, 15, 16, 17, 18, 19, 20, 24, 28, 32, 36, 40, 44, 48, 52, 56, 60 weeks or longer.

In an aspect, an initial dose/injection or starting dose/injection of Nle-substituted, other amino acid substituted Pro-hIFN A2b, Pro-hIFN A2b, and/or mixture thereof refers to the first dose administered to a subject for treating myelofibrosis of any subtype (e.g., idiopathic, primary, and/or early), polycythemia vera (high or low risk), essential thrombocythaemia, and/or chronic myeloid leukemia during a treatment period (i.e., week 0), wherein, prior to the treatment period, the subject is interferon-treatment naïve or has not been administered the same active ingredient as Nle-substituted, other amino acid substituted Pro-hIFN A2b, Pro-hIFN A2b, and/or mixture thereof. A subject who is interferon-treatment naïve is a subject who has not been treated with any form of interferon, whether pegylated or non-pegylated.

In another embodiment, all of the above recited dosages for treating myelofibrosis of any subtype (e.g., idiopathic, primary, and/or early), polycythemia vera (high or low risk), essential thrombocythaemia, and/or chronic myeloid leukemia can be administered per dose, and/or per injection. Non-limiting example include administering about 250-350-500 μg of drug using about 50 μg per about 5 injections at about the same time and/or different times, so long as the subject receives a total of about 250 μg dose, or about 100

μg per injection about 5 times at about the same time and/or different times for a total of about 500 μg dose. The combination can be picked and choose depending on patient or subject convenience and/or medical need. In another non-limiting example, the entire about 250 μg can be all administered in a single injection (per injection) at a single time point for the desired 250 μg dose.

In an embodiment, any of the above-mentioned dosage, or dosage scheme can be use, and/or in a mix-and-match fashion for treating myelofibrosis of any subtype (e.g., idiopathic, primary, and/or early), polycythemia vera (high or low risk), essential thrombocythaemia, and/or chronic myeloid leukemia, depending on the subject's tolerance and a physician's assessment (e.g., based on number and/or types of AE). In another embodiment, all of the above recited dosages can be administered per dose, and/or per injection. Non-limiting example include administering about 250 ug, 350 ug of drug using about 600 ug per about 3 injections at about the same time and/or different times, so long as the subject receives a total of about 600 ug dose. The combination can be picked and choose depending on patient or subject convenience and/or medical need. In another non-limiting example, the entire about 600 ug can be all administered in a single injection (per injection) at a single time point.

Administration Methods

In an aspect, Nle-substituted, other amino acid substituted Pro-hIFN A2b, Pro-hIFN A2b, and/or mixture thereof can be used for subcutaneous injection to a subject. Alternative, or additionally, Nle-substituted, other amino acid substituted Pro-hIFN A2b, Pro-hIFN A2b, and/or mixture thereof can be administered for treating myelofibrosis of any subtype (e.g., idiopathic, primary, and/or early), polycythemia vera (high or low risk), essential thrombocythaemia, and/or chronic myeloid leukemia via topical contact, intravenous, intraperitoneal, intramuscular, intralesional, intranasal or the implantation of a slow-release device e.g., a mini-osmotic pump, to a subject. Other administration is by any route including parenteral, and transmucosal (e.g., oral, nasal, vaginal, rectal, or transdermal). Parenteral administration includes, e.g., intravenous, intramuscular, intra-arteriole, intradermal, intraperitoneal, intraventricular, and/or intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches.

Depending on the desired purpose(s), the pharmaceutical composition or medicament in accordance with the present disclosure can also be provided in other forms. For example, the pharmaceutical composition or medicament can be provided in a form for oral administration, intravenous injection (including drip infusion and bolus injection), intramuscular injection, subcutaneous injection, intraarterial injection, intraperitoneal injection, transdermal administration (such as a patch), or transmucosal administration (such as nasal spray, nasal drops, and suppository), but is not limited thereby. Depending on the form and purpose(s), a carrier can be chosen and used to provide the pharmaceutical composition or medicament, wherein the carriers are known in the art. Examples of the carrier include, but are not limited to, excipients, diluents, fillers, buffers, auxiliaries, stabilizers, absorption enhancers, disintegrating agents, hydrotropic agents, antioxidants, adhesives, binders, tackifiers, dispersants, suspending agents, lubricants, and hygroscopic agents.

In an embodiment, as a form for oral administration, the pharmaceutical composition or medicament in accordance with the present disclosure can be provided by any methods in any form for oral administration, wherein the liquid form suitable for oral administration includes syrups, an oral solution, a suspension, and an elixir, and the solid form suitable for oral administration includes a powder, a granule, a troche, a dragee, an enteric-coated tablet, a chewable tablet, an effervescent tablet, a film-coated tablet, a capsule, and a long-acting slow-release tablet. The pharmaceutical composition or medicament provided in accordance with the present disclosure can comprise any pharmaceutically acceptable carrier that will not adversely affect the desired effects of the active ingredient (i.e., antibodies of the present disclosure or antigen-binding fragment thereof). For example, the pharmaceutically acceptable carriers for the aforesaid liquid form include but are not limited to, water, saline, dextrose, glycerol, ethanol or its analogs, oil (e.g., olive oil, castor oil, cottonseed oil, peanut oil, corn oil, and germ oil), glycerol, polyethylene glycol, and combinations thereof, and the pharmaceutically acceptable carriers for the aforesaid solid form include, but are not limited to, cellulose, starch, kaolinite, bentonite, sodium citrate, gelatin, agar, carboxymethyl cellulose, gum arabic, tragacanth, seaweed gel, glyceryl monostearate, calcium stearate, colloidal silicon dioxide, and combinations thereof.

In another embodiment, as a form for transdermal administration, the pharmaceutical composition or medicament in accordance with the present disclosure can also comprise any pharmaceutically acceptable carrier that will not adversely affect the desired effects of the active ingredient (i.e., antibodies of the present disclosure or antigen-binding fragment thereof), such as water, mineral oil, propylene glycol, polyethylene oxide, liquid petrolatum, sorbitan monostearate, and polysorbate 60. The pharmaceutical composition or medicament can be provided by any suitable methods in any suitable form for transdermal administration, such as in the form of a patch (such as a microneedle patch), but is not limited thereby.

As for the form of injections or drips, the pharmaceutical composition or medicament can comprise one or more ingredient(s), such as an isotonic solution, a salt-buffered saline (e.g., phosphate-buffered saline or citrate-buffered saline), a hydrotropic agent, an emulsifier, a 5% sugar solution, and other carriers to provide the pharmaceutical composition or medicament as an intravenous infusion, an emulsified intravenous infusion, a powder for injection, a suspension for injection or a powder suspension for injection. Alternatively, the pharmaceutical composition or medicament can be prepared as a pre-injection solid. The desired injection is provided by dissolving the pre-injection solid in other solutions or suspensions or emulsifying it before being administered to a subject or subject in need.

In an embodiment, as a form for transmucosal administration, the pharmaceutical composition or medicament can comprise one or more ingredient(s), such as a penetrant, a surfactant, a viscosity regulator, a pH-adjusting agent, a preservative, a stabilizer, an osmo-regulator, and other carriers to provide the pharmaceutical composition or medicament as eye drops, an ointment, orally disintegrating tablets, a nasal spray, nasal drops, or a suppository.

Optionally, the pharmaceutical composition or medicament in accordance with the present disclosure can also comprise an amount of additives, such as a toner or a colorant for enhancing the visual perception of the pharmaceutical composition or medicament, and/or a buffer, a conservative, a preservative, an antibacterial agent, or an antifungal agent for improving the stability and storability of the pharmaceutical composition or medicament.

In certain embodiments, Nle-substituted, other amino acid substituted Pro-hIFN A2b, Pro-hIFN A2b, and/or mixture thereof is administered for treating myelofibrosis of any subtype (e.g., idiopathic, primary, and/or early), polycythemia vera (high or low risk), essential thrombocythaemia, and/or chronic myeloid leukemia once daily, about once weekly, about once every two weeks, about once every three weeks, about once every four weeks, about once every five weeks, about once every six weeks, or about once every three months. Nle-substituted, other amino acid substituted Pro-hIFN A2b, Pro-hIFN A2b, and/or mixture thereof can be co-administered within about twenty-four hours of a dose of chemotherapy and/or radiation therapy.

In certain embodiments, Nle-substituted, other amino acid substituted Pro-hIFN A2b, Pro-hIFN A2b, and/or mixture thereof is co-administered at least once about 3, once about 7, once about 10, once about 14, once about 17 or once about 21 days before a dose of chemotherapy and/or radiation therapy. In an embodiment, Nle-substituted, other amino acid substituted Pro-hIFN A2b, Pro-hIFN A2b, and/or mixture thereof can be co-administered to a patient immediately after, at about the same time, and/or any time during chemo and/or radiation therapy.

Uses

In one embodiment, Nle-substituted, other amino acid substituted Pro-hIFN A2b, Pro-hIFN A2b, and/or mixture thereof can be used to treat a subject with myelofibrosis of any subtype (e.g., idiopathic, primary, and/or early), polycythemia vera (high or low risk), essential thrombocythaemia, and/or chronic myeloid leukemia of any subtype.

Yet in another embodiment, the existence of any of one or more Nle-substituted Pro-hIFN A2b of Pro-hIFN A2b at Met17, Met 22, Met60, Met112, and/or Met149 positions indicate that the any part of the present method, in part or in whole, of making Pro-hIFN a2b was utilized.

Yet in another embodiment, the existence of any of one or more Nle-substituted Pro-hIFN A2b of Pro-hIFN A2b at Met17, Met 22, and/or Met149 positions indicate that the any part of the present method, in part or in whole, of making Pro-hIFN a2b was utilized.

In another embodiment, the existence of an amino acid substitution from Gly 45 to Asp of Pro-hIFN A2b indicates that any part of the present method of making Pro-hIFN a2b was utilized.

Yet in another embodiment, the existence of any of one or more Nle-substituted Pro-hIFN A2b of Pro-hIFN A2b at Met17, Met 22, Met60 Met112, Met149 positions indicate, in addition to the existence of either of amino acid substitution from Gly 45 to Asp or Asn 66 to Lys of Pro-hIFN A2b indicates that the any part of the present method of making Pro-hIFN a2b, in part or in whole, was utilized.

In another embodiment, the existence of an amino acid substitution from Asn 66 to Lys of Pro-hIFN A2b indicates that any part of the present method of making Pro-hIFN a2b, in part or in whole, was utilized.

In another embodiment, the existence of amino acid substitutions from Gly 45 to Asp and Asn 66 to Lys of Pro-hIFN A2b indicates that any part of the present method of making Pro-hIFN a2b, in part or in whole, was utilized.

In another embodiment, the existence of amino acid substitutions from Gly 45 to Asp and Asn 66 to Lys of Pro-hIFN A2b at a quantitative ratio of about 1:3, 1:4, 1:5, 1:6, and/or 1:7 or any variations thereof, which indicate that any part the present method of making Pro-hIFN a2b, in part or in whole, was utilized.

In another embodiment, the Nle substituted Pro-hIFN alpha 2b comprises: Nle substitution at position 60 for Methionine and Asp substitution at position 45 for Gly; Nle substitution at position 60 for Methionine and Lys substitution at position 66 for Asn; Nle substitution at position 60 for Methionine, Asp substitution at position 45 for Gly and Lys substitution at position 66 for Asn; Nle substitution at position 112 for Methionine Asp substitution at position 45 for Gly; Nle substitution at position 112 for Methionine Lys substitution at position 66 for Asn; Nle substitution at position 112 for Methionine Asp substitution at position 45 for Gly and Lys substitution at position 66 for Asn; Nle substitution at position 60 for Methionine, Nle substitution at position 112 for Methionine and Asp substitution at position 45 for Gly; Nle substitution at position 60 for Methionine, Nle substitution at position 112 for Methionine Lys substitution at position 66 for Asn; or Nle substitution at position 60 for Methionine, Nle substitution at position 112 for Methionine Asp substitution at position 45 for Gly and Lys substitution at position 66 for Asn. In another embodiment, the existence of any amino acid or Nle substituted Pro-hIFN A2b at any quantitative ratio, any variations thereof, indicate that any part the present method of making Pro-hIFN a2b, in part or in whole, was utilized.

In an embodiment, at this stage, the mere fact that the detection of existence of Nle at Met 60, Met 112 or Asp45/Lsy66 in any ratio indicates the any part manufacturing method, in part of in whole, of the present disclosure was used. In another embodiment, the detection ratio before or after any manufacturing step(s) of the present disclosure between the amount of Gly 45 to Asp, and Asn 66 to Lys may be about 1:1, 1:2, 1:3, 1:4, 1:5, 2:1, 3:1, 4:1, 5:1, or any variation thereof, indicates any part of the present disclosure's method, in part of in whole, was utilized.

Yet in another embodiment, the mere fact that the detection of existence of Nle at Met 60, Met 112 before or after any manufacturing step(s) of the present disclosure at the ratio of about 1:1, 1:2, 1:3, 2:1, 3:1, or any variations thereof also indicates any part of the present disclosure's method, in part of in whole, was utilized.

Yet in another embodiment, the mere fact that the detection of existence of Nle at Met 17, Met 22 of Pro-hIFN alpha 2b before or after any manufacturing step(s) of the present disclosure at the ratio of about 1:1, 1:2, 1:3, 2:1, 3:1, or any variations thereof also indicates any part of the present disclosure's method, in part of in whole, was utilized.

Surprising Advantages and/or Improvement

Norleucine (abbreviated as Nle) is an amino acid with the formula $CH_3(CH_2)_3CH(NH_2)CO_2H$. A systematic name for this compound is 2-aminohexanoic acid. The compound is an isomer of the more common amino acid leucine. Nle biosynthesis and Nle substitution at the protein level dependent on the host expression system. It was reported that non-standard amino acid biosynthesis and incorporation were substantially reduced when *E. coli* BL21(DE3) was used instead of *E. coli* K12 (see for example, Ni et al., *J Ind Microbiol Biotechnol* (2015) 42:971-975). In the present disclosure, in an embodiment, BL21(DE3) or BLR-(DE3)-RIL was one example used. Therefore, the existing and detection of Nle substitution was surprising and unexpected.

In addition, as compared to the previously reported method of making Pro-hIFN alpha 2b (see U.S. Pat. No. 8,106,160, the contents are all incorporated herein in their entirety), the present disclosure's method production of Pro-hIFN alpha 2b with and/or without Nle-substituted, other amino acid substituted Pro-hIFN A2b, Pro-hIFN A2b, and/or mixture thereof can be used as an indicator that the present disclosure's method of making, in part of in whole, was utilized and/or performed. For example, see FIG. 3 of U.S. Pat. No. 8,106,160, and/or the lack of known Nle-substituted, other amino acid substituted Pro-hIFN A2b, Pro-hIFN A2b, and/or mixture thereof in the art.

In addition, in another embodiment, not all Met have Nle incorporation and/or amino acid substitution.

Further, in an embodiment Nle-substituted, amino acid substituted Pro-hIFN A2b, and/or mixture thereof does not always present in a given batch of manufacturing. In an occasion, Nle-substituted, other amino acid substituted Pro-hIFN A2b, and/or mixture thereof was/were not detected. In other embodiment, Nle-substituted, amino acid substituted Pro-hIFN A2b, and/or mixture thereof can be detected at frequencies 90%, 91%, 92%, 93%, 94%, 95%, 96%, 97%, 98%, 99%, 99.5%, 99.9% and/or 99.99% over time.

In an embodiment, one or more Nle substituted Pro-hIFN alpha 2b are located at the any combinations of the positions at Met17, Met22, Met60, Met112, and/or Met149. Alternatively, or additionally, Pro-hIFN alpha 2b also includes amino acid substitution of Gly 45 to Asp and/or Asn 66 to Lys.

In an embodiment, one or more Nle substituted Pro-hIFN alpha 2b are located at the any combinations of the positions at Met17, Met22, and/or Met149.

In an embodiment, two, three, four or more Nle substituted Pro-hIFN alpha 2b are located at the any combinations of the positions at Met17, Met22, Met60, Met112, and Met149.

In an embodiment, two, or three Nle substituted Pro-hIFN alpha 2b are located at the any combinations of the positions at Met17, Met22, and Met149.

Yet in an embodiment, the substituted amino acid position of Pro-hIFN alpha 2b is from Gly 45 to Asp.

Yet in another embodiment, the substituted amino acid position of Pro-hIFN alpha 2b is from Asn 66 to Lys.

In another embodiment, the substituted amino acid position of Pro-hIFN alpha 2b is from Gly 45 to Asp and Asn 66 to Lys.

In an embodiment, the ratio of Gly 45 to Asp and Asn 66 to Lys amount is about 1:3, about 1:4, about 1:5, about 1:6, about 1:7, about 1:8, about 1:9, and/or about 1:10.

Yet in another embodiment, the Pro-hIFN alpha 2b can have Nle substitution at amino acid Met 60, Met 112, substitutions from Gly 45 to Asp, and substitutions from Asn 66 to Lys.

In an embodiment, the Nle substituted Pro-hIFN alpha 2b comprises: Nle substitution at position 60 for Methionine and Asp substitution at position 45 for Gly; Nle substitution at position 60 for Methionine and Lys substitution at position 66 for Asn; Nle substitution at position 60 for Methionine, Asp substitution at position 45 for Gly and Lys substitution at position 66 for Asn; Nle substitution at position 112 for Methionine Asp substitution at position 45 for Gly; Nle substitution at position 112 for Methionine Lys substitution at position 66 for Asn; Nle substitution at position 112 for Methionine Asp substitution at position 45 for Gly and Lys substitution at position 66 for Asn; Nle substitution at position 60 for Methionine, Nle substitution at position 112 for Methionine and Asp substitution at position 45 for Gly; Nle substitution at position 60 for Methionine, Nle substitution at position 112 for Methionine Lys substitution at position 66 for Asn; or Nle substitution at position 60 for Methionine, Nle substitution at position 112 for Methionine Asp substitution at position 45 for Gly and Lys substitution at position 66 for Asn.

EXAMPLES

Example 1

Preparation of Recombinant N-Terminal Modified hIFN-α2b

This method is not identical to known method of making Pro-hIFN A2b. Here, a nucleic acid encoding Pro-hIFN-α2b was obtained by amplifying hIFN-α2b using primers. Briefly, codons, ATG and CCG (encoding Met and Pro, respectively) were added to the 5' of coden that encodes Cys of mature hIFN-α2b. This nucleic acid was cloned into expression vector pET-24a.

pET-24a vectors, carrying the Pro-hIFN-α2b genes, were then transformed into *E. coli* BL21 such as BLR-(DE3)-RIL or BL21(DE3) strain. *E. coli* clones expressing high levels of the protein were selected. The nascent protein expressed from the Pro-hIFN-α2b gene has a Met at its N-terminus (Met-Pro-Cys-). This Met residue was removed in *E. coli* via internal enzymatic digestion, resulting in a mature protein having an N-terminal Pro, which is linked to the Cys1 of hIFN-α2b (Pro-Cys-).

The *E. coli* clone which will express Pro-hIFN-α2b was cultured in a 1000 ml flask containing about 250 ml SYN Broth medium (soytone, yeast extract, and NaCl) with kanamycin (50 ug/mL) and chloramphenicol (50 ug/mL) at 37° C., rotated at 200 rpm for between about 14-16 hours overnight. About 220 ml of the overnight culture were then transferred to a 5-liter jar fermenter containing 3 L define medium (10 μg/L glucose, 0.7 μg/L $MgSO_4 \cdot 7H_2O$, 4 μg/L $(NH_4)2HPO_4$, 3 μg/L $KH_2PO_4$, 6 μg/L $K_2HPO_4$, 1.7 μg/L citrate, 10 μg/L yeast extract, 10 ml/L Trace Element, and 2 μg/L isoleucine) with kanamycin (25 ug/mL), chloramphenicol (25 ug/mL), 0.4% glycerol, and 0.5% (v/v) trace elements (10 μg/L of $FeSO_4 \cdot 7H_2O$, 2.25 μg/L of $ZnSO_4 \cdot 7H_2O$, 1 μg/L of $CuSO_4 \cdot 5H_2O$, 0.5 μg/L of $MnSO_4 \cdot H_2O$, 0.3 μg/L of $H_3BO_3$, 2 μg/L of $CaCl_2 \cdot 2H_2O$, 0.1 μg/L of $(NH_4)6Mo7O_{24}$, about 0.81 to 0.84 μg/L EDTA, and 50 ml/L HCl). The oxygen concentration in the medium was controlled at about 40%, between about 40 to 45%, or above about 45% and its pH maintained at between about 6.9-7.1 by adding about between 25% to 37% ammonia water whenever necessary. A feeding solution containing between about 600-800 μg/L of glucose and about 20 μg/L of $MgSO_4 \cdot 7H_2O$ was prepared. When the dissolved oxygen rose to a value greater than the set point, an appropriate volume of the feeding solution was added to increase the glucose concentration in the culture medium. The expression of the Pro-hIFN-α2b gene was induced by IPTG at a final concentration of between about 0.6-0.8 mM, then addition of feeding material (yeast extract and trace element). *E. coli* cells expressing these proteins were collected post five hours after IPTG induction.

The collected *E. coli* cells were resuspended in TEN buffer (50 mM Tris-HCl, pH 7.0; 1 mM EDTA, and 100 mM NaCl) in a ratio of between about 1:2, 1:3, 1:4, or 1:5 to 1:10 (wet weight g/mL), disrupted by a homogenizer, and then centrifuged at between about 5,000 to 10,000 rpm for between about 20 to 40 min. The pellet containing inclusion bodies (IBs) was washed twice with TEN buffer and centrifuged as described above, suspended in a ratio of between about 0.8 to 1.2 ml solution: between about 1.8 to 2.7 μg pellet wet weight g/mL of a between about 3-4 M guanidium HCl (GnHCl) aqueous solution, and then centrifuged at about 5,000 rpm for about 15 min. The IBs, containing recombinant hIFN-α2b, were then solubilized in 50 mL of between about 5-6 M GuHCl with about 5 mM DTT, which was then stirred at room temperature for about 1.5 hr followed by centrifugation at about 20,000 rpm for about 20 min at about 25° C. The supernatant was collected. In this process, the recombinant Pro-hIFN A2b (and/or acetylated Pro-hIFN A2b) protein was denatured.

At this stage, the mere fact that the detection of existence of Nle at Met17, Met22, Met 60, Met 112, Met149 and/or substitution at Asp45/Lsy66 of Pro-hIFN A2b in any amount and/or ratio indicates the manufacturing method of the present disclosure, in part or in whole, was used. In addition, the mere fact that the detection of existence of Nle at Met17, Met22, and/or Met149 of Pro-hIFN A2b in any amount and/or ratio indicates the manufacturing method of the present disclosure, in part or in whole, was used. The detection ratio before or after any manufacturing step(s) of the present disclosure between the amount of Gly 45 to Asp, and Asn 66 to Lys was about 1:1, 1:2, 1:3, 1:4, 1:5, 2:1, 3:1, 4:1, 5:1, or any variation thereof, indicates any part of the present disclosure's method was utilized.

In addition, the mere fact that the detection of existence of Nle at Met 60, Met 112 before or after any manufacturing step(s) of the present disclosure at the ratio of about 1:1, 1:2, 1:3, 2:1, 3:1, or any variations thereof also indicates any part of the present disclosure's method was utilized.

Example 2

Gel Electrophoresis

The protein concentration of the crude lysate was determined by BCA protein assay, and the Pro-hIFN A2b was determined by isoelectric focusing gel electrophoresis. The charge distribution of Pro-IFN alfa-2b was also evaluated by isoelectric focusing (IEF) gel electrophoresis. The results are illustrated in FIG. 3, with duplicated lanes each loaded with about 15 ug with a marker line loaded with about 10 uL on the very left labelled as "M". FIG. 3 shows an IEF profile that gives major band with the isoelectric point (pI) of 6.1 for Pro-IFN alfa-2b. Results are consistent with the detection of an IEF main band at pI 6.1±0.1.

At this stage, the mere fact that the detection of existence of Nle at Met 60, Met 112 or Asp45/Lsy66 in any ratio indicates the manufacturing method of the present disclosure was used. In addition, the mere fact that the detection of existence of Nle at Met17, Met22, and/or Met149 of Pro-hIFN A2b in any amount and/or ratio indicates the manufacturing method of the present disclosure, in part or in whole, was used. The detection ratio before or after any manufacturing step(s) of the present disclosure between the amount of Gly 45 to Asp, and Asn 66 to Lys may be about 1:1, 1:2, 1:3, 1:4, 1:5, 2:1, 3:1, 4:1, 5:1, or any variation thereof, indicates any part of the present disclosure's method was utilized.

In addition, the mere fact that the detection of existence of Nle at Met 60, Met 112 before or after any manufacturing step(s) of the present disclosure at the ratio of about 1:1, 1:2, 1:3, 2:1, 3:1, or any variations thereof also indicates any part of the present disclosure's method was utilized.

Example 3

Refolding of Pro-hIFN Alpha 2b.

The above-described IBs were mixed with 1.5 L freshly prepared refolding buffer (100 mM Tris-HCl (pH 7.0), 0.5 M L-Arginine, 2 mM EDTA). The reaction mixture thus formed was incubated for between about 24~36 hr. without stirring at room temperature to allow refolding of the recombinant Pro-hIFN alpha 2b.

At this stage, whether the protein is in denatured or folded, the mere fact that any detection of existence of Nle at Met17, Met22, Met60, Met112, Met149 and/or substitution at Asp45/Lsy66 of Pro-hIFN alpha 2b in any amount and/or ratio indicates the manufacturing method of the present disclosure was used. In addition, the mere fact that the detection of existence of Nle at Met17, Met22, and/or Met149 of Pro-hIFN A2b in any amount and/or ratio indicates the manufacturing method of the present disclosure, in part or in whole, was used. The detection ratio before or after any manufacturing step(s) of the present disclosure between the amount of Gly 45 to Asp, and Asn 66 to Lys may be about 1:1, 1:2, 1:3, 1:4, 1:5, 2:1, 3:1, 4:1, 5:1, or any variation thereof, indicates any part of the present disclosure's method was utilized.

In addition, whether the protein is in denatured or fled stage, the mere fact that the detection of existence of Nle at Met17, Met22, Met149 of Pro-hIFN alpha 2b before or after any manufacturing step(s) of the present disclosure at the ratio thereof also indicates any part of the present disclosure's method was utilized. Further, whether the protein is in denatured or fled stage, the mere fact that the detection of existence of Nle at Met60 and Met112, before or after any manufacturing step(s) of the present disclosure at the ratio of about 1:1, 1:2, 1:3, 2:1, 3:1, or any variations thereof also indicates any part of the present disclosure's method was utilized.

Example 4

Ultrafiltration/Diafiltration

This method is not identical compared to known method of making Pro-hIFN A2b. Here the refolded mixture was centrifuged under about 10,000±1,000 rpm at room temperature. The collected supernatant was filtered through 0.2 m filters and clarified solution was obtained. The filtrate was then concentrated 20 folds by a tangential Ultrafiltration system and diafiltered in constant-volume-mode with about 7 volumes of Q-A equilibrium buffer (about pH 7.0±0.1, conductivity<2 mS/cm). Finally, the retentate suspension was harvested. The suspension was then centrifuged at between about 8000-9,000 rpm, about 15-25 min at 4° C. The collected supernatant was then pumped through a Sartorius 0.2 m filter. A volume of about 10-20 mL sample was taken out for protein concentration analysis by the BCA method. The filtrate was obtained and stored in refrigerator overnight at 4° C.

At this stage, the mere fact that the detection of existence of Nle at Met17, Met22, Met60, Met112, Met149 and/or substitution of Asp45/Lsy66 of Pro-hIFN alpha 2b in any amount or ratio indicates the manufacturing method of the present disclosure was used. In addition, the mere fact that the detection of existence of Nle at Met17, Met22, and/or Met149 of Pro-hIFN A2b in any amount and/or ratio indicates the manufacturing method of the present disclosure, in part or in whole, was used. Further, the detection ratio before or after any manufacturing step(s) of the present disclosure between the amount of Gly 45 to Asp, and Asn 66 to Lys may be about 1:1, 1:2, 1:3, 1:4, 1:5, 2:1, 3:1, 4:1, 5:1, or any variation thereof, indicates any part of the present disclosure's method was utilized.

In addition, the mere fact that the detection of existence of Nle at Met 60, Met 112 before or after any manufacturing step(s) of the present disclosure at the ratio of about 1:1, 1:2, 1:3, 2:1, 3:1, or any variations thereof also indicates any part of the present disclosure's method was utilized.

Example 5

Ammonium Acetate/Sulfate Precipitation (AAP/ASP)

This example is another illustration of departure of known method of making Pro-hIFN alpha 2b. Here a buffer for ammonium acetate precipitation was prepared to contain about 48 μg/L ammonium acetate (about 0.6 M $NH_4OAc$) and about 180 μg/L sodium chloride at about pH 2.8. The precipitation was performed by adding 40 ml AAP buffer to Pro-hIFN alpha 2b in glass bottle with stirring. The solution was then placed in 40° C. water bath and incubated for about 2 h. After incubation, the mixture was then clarified by centrifugation at about 9,000 rpm for about 20 min at 4° C. The pooled supernatant was adjusted to pH about 4.5. After the pooled supernatant was filtered by 0.2 m filtration membrane, the filtrate was stored at 4° C. overnight.

At this stage, the mere fact that the detection of existence of Nle at Met17, Met22, Met60, Met112, Met149, and/or substitution of Asp45/Lsy66 of Pro-hIFN alpha 2b in any amount or ratio indicates the manufacturing method of the present disclosure, in part or in whole, was used. In addition, the mere fact that the detection of existence of Nle at Met17, Met22, and/or Met149 of Pro-hIFN A2b in any amount and/or ratio indicates the manufacturing method of the present disclosure, in part or in whole, was used.

The detection ratio before or after any manufacturing step(s) of the present disclosure between the amount of Gly 45 to Asp, and Asn 66 to Lys may be about 1:1, 1:2, 1:3, 1:4, 1:5, 2:1, 3:1, 4:1, 5:1, or any variation thereof, indicates the present disclosure's method, in part or in whole, was utilized.

In addition, the mere fact that the detection of existence of Nle at Met 60, Met 112 before or after any manufacturing step(s) of the present disclosure at the ratio of about 1:1, 1:2, 1:3, 2:1, 3:1, or any variations thereof also indicates the present disclosure's method, in part or in whole, was utilized.

Example 6

Purification (Anionic Exchange, AIX)

AIX column flow rate was at about 35 ml/min. there are two washing steps in before elution. The elution step were performed at 15 about CV of elution buffer containing about 80 mM NaCl was used. The elution of Pro-hIFN alpha 2b, amino acid substituted Pro-hIFN alpha 2b, Nle substituted Pro-hIFN alpha 2b, or mixture thereof were all monitored by 280 nm UV detection. The wash condition is set at between 15-25 mM of wash salt solution, and the elution buffer has the salt concentration of between 75-85 mM. pH is maintained at about 7.

At this stage, the mere fact that the detection of existence of Nle at Met17, Met22, Met60, Met 112, Met149, and/or or Asp45/Lsy66 of Pro-hIFN alpha 2b in any amount or ratio indicates the manufacturing method of the present disclosure was used. In addition, the mere fact that the detection of existence of Nle at Met17, Met22, and/or Met149 of Pro-hIFN A2b in any amount and/or ratio indicates the manufacturing method of the present disclosure, in part or in whole, was used.

The detection ratio before or after any manufacturing step(s) of the present disclosure between the amount of Gly 45 to Asp, and Asn 66 to Lys may be about 1:1, 1:2, 1:3, 1:4, 1:5, 2:1, 3:1, 4:1, 5:1, or any variation thereof, indicates any part of the present disclosure's method was utilized.

In addition, the mere fact that the detection of existence of Nle at Met 60, Met 112 before or after any manufacturing step(s) of the present disclosure at the ratio of about 1:1, 1:2, 1:3, 2:1, 3:1, or any variations thereof also indicates any part of the present disclosure's method was utilized.

Example 7

N-Terminal Sequencing and Peptide Mapping of Pro-IFN-α2b

The tested sample was subjected to Edman degradation chemistry that uses phenylisothiocyanate to react with the uncharged N-terminal amino group on the protein sample. The resulting phenylthiohydantoin (PTH)-amino acid derivative is stable and can be identified by RP-HPLC.

Peptide mapping was employed to analyze the sequence of Pro-IFN alfa-2b. Peptide maps were generated by the RP-HPLC separation of peptide mixtures resulting either from trypsin and endoproteinase Lys-C dual-digestion or from endoproteinase Glu-C digestion of a sample. After the digestion, the proteolytic reaction was quenched by the addition of trifluoroacetic acid (TFA). The resulting peptide mixtures were separated using RP-HPLC with TFA/acetonitrile (ACN) gradient to generate a non-reduced map. To obtain a reduced map, peptide mixtures were reduced with tris (2-carboxyethyl) phosphine hydrochloride (TCEP-HCl) after the reaction is quenched and then subjected to RP-HPLC. The eluted peptide peaks were monitored by UV detection and subsequently analyzed by on-line LC-MS/MS for detection of peptide masses and sequence of selected peptides.

Trypsin/Lys-C Peptide Mapping

The protein sample was digested with trypsin in sodium phosphate buffer. Next, an aliquot of Lysyl Endopeptidase (Lys-C) was added to the tryptic digested peptide mixture. The reaction was quenched by adding trifluoroacetic acid (TFA). The mixture was subsequently reduced by tris (2-carboxyethyl) phosphine hydrochloride (TCEP-HCl).

Table 1 summarizes the identification of all peptides obtained from the reduced trypsin/Lys-C peptide map. All expected peaks with respective sequence assignment and measurement of accurate masses are observed except for short peptide fragments that are not recoverable on the maps. These fragments contain only a single residue or dipeptides, such as T2, T4, T6, T12, T15, T16, T20, and T21; and some of them can be identified in partially digested long peptides such as T2-3, T6-7, T12-13 and T16-17.

TABLE 1

| Peptide | Residue | Sequence | Monoisotopic Mass (cal.) | observed mass |
|---|---|---|---|---|
| T1 | 1-13 | PCDLPQTHSLGSR | 1409.67 | *1409.68* |
| T1a | 1-8 | PCDLPQTH | 909.40 | *969.41* |

TABLE 1-continued

| Peptide | Residue | Sequence | Monoisotopic Mass (cal.) | observed mass |
|---|---|---|---|---|
| T2 | 14 | R | 174.11 | ND |
| T3 | 15-23 | TLMLLAQMR | 1075.59 | *1075.60* |
| T4 | 24 | R | 174.11 | ND |
| T5 | 25-32 | ISLFSCLK | 909.50 | *909.51* |
| T6 | 33-34 | DR | 289.14 | ND |
| T7 | 35-50 | HDFGFPQEEFGNQFQK | 1953.86 | *1953.87* |
| T6-7 | 33-50 | DRHDFGFPQEEFGNQFQK | 2224.99 | *2225.00* |
| T8 | 51-71 | AETIPVLHEMIQQIFNLFSTK | 2458.29 | *2458.31* |
| T9 | 72-84 | DSSAAWDETLLDK | 1449.66 | *1449.67* |
| T10 | 85-113 | FYTELYQQLNDLEACVIQGVGVTETPLMK | 3301.63 | *3301.63* |
| T11 | 114-121 | EDSILAVR | 901.49 | *901.50* |
| T12 | 122 | K | 146.11 | ND |
| T13 | 123-126 | YFQR | 612.30 | *612.31* |
| T12-13 | 122-126 | KYFQR | 740.40 | *740.41* |
| T14 | 127-132 | ITLYLK | 749.47 | *749.48* |
| T15 | 133-134 | EK | 275.15 | ND |
| T16 | 135 | K | 146.11 | ND |
| T17 | 136-345 | YSPCAWEVWR | 1208.57 | *1208.58* |
| T16-17 | 134-145 | KYSPCAWEVVR | 1336.66 | *1336.67* |
| T18 | 146-150 | AEIMR | 618.32 | *618.32* |
| T19 | 151-163 | SFSLSTNLQESLR | 1480.75 | *1480.76* |
| T20 | 164-165 | SK | 233.14 | ND |
| T21 | 166 | E | 147.05 | ND |

At this stage, the mere fact that the detection of existence of Nle at Met17, Met22, Met60, Met112, Met149 and/or substitution at Asp45/Lsy66 of Pro-hIFN alpha 2b in any ratio indicates the manufacturing method of the present disclosure, in part or in whole, was used. In addition, the mere fact that the detection of existence of Nle at Met17, Met22, and/or Met149 of Pro-hIFN A2b in any amount and/or ratio indicates the manufacturing method of the present disclosure, in part or in whole, was used.

The detection ratio before or after any manufacturing step(s) of the present disclosure between the amount of Gly 45 to Asp, and Asn 66 to Lys can be about 1:1, 1:2, 1:3, 1:4, 1:5, 2:1, 3:1, 4:1, 5:1, or any variation thereof, indicates any part of the present disclosure's method was utilized.

In addition, the mere fact that the detection of existence of Nle at Met 60, Met 112 before or after any manufacturing step(s) of the present disclosure at the ratio of about 1:1, 1:2, 1:3, 2:1, 3:1, or any variations thereof also indicates any part of the present disclosure's method was utilized.

Example 8

Multiple runs of making and analyzing Pro-IFN-α2b disclosed in Examples 1-7 were performed. Unexpected detection and analysis of Pro-IFN-α2b with Nle incorporation and unexpected detection and analysis of Pro-IFN-α2b with Nle substitution and/or other substitutions or mixtures thereof.

Although peptide mapping showed correct amino acid sequences, the same was further analyzed with reverse phase HPLC and IEX-HPLC.

The Pro-IFN alfa-2b RP-HPLC resolved Pro-IFN alfa-2b sample which contains modified IFN species including Nle 112 and Nle 60. In another run, all 5 Nle at position 60, 112, 17, 22 and 149 of Pro-IFN alfa-2b were present. Yet in another run, 3 Nle at position 17, 22 and 149 of Pro-IFN alfa-2b were present. Nonetheless, Nle is not produced all the time in certain runs. Furthermore, substitution at Asp45/Lsy66 do occur, but not always present.

As stated above, Norleucine (abbreviated as Nle) is an amino acid with the formula $CH_3(CH_2)_3CH(NH_2)CO_2H$. A systematic name for this compound is 2-aminohexanoic acid. The compound is an isomer of the more common amino acid leucine. It is known in the art that the level of Nle biosynthesis and Nle substitution at the protein level dependent on the host expression system. It was further reported that non-standard amino acid biosynthesis and incorporation were substantially reduced when *E. coli* BL21(DE3) was used instead of *E. coli* K12 (see for example, Ni et al., *J Ind Microbiol Biotechnol* (2015) 42:971-975). In this example, the BL21(DE3) was used. Therefore, the existing and detection of Nle substitution and/or other amino acid substitutions were surprising and unexpected.

The observed major mass signal is 19362 Da which matches the expected Pro-IFN alfa-2b mass of 19362 Da. Masses with lower signal was also present. A species with the molecular weight centered at 19344 Da is noted, which is 18 Da less than the main Pro-IFN alfa-2b product. The mass corresponds to Pro-IFN alfa-2b variant forms with norleucine incorporation in place of methionine.

Figure 4:
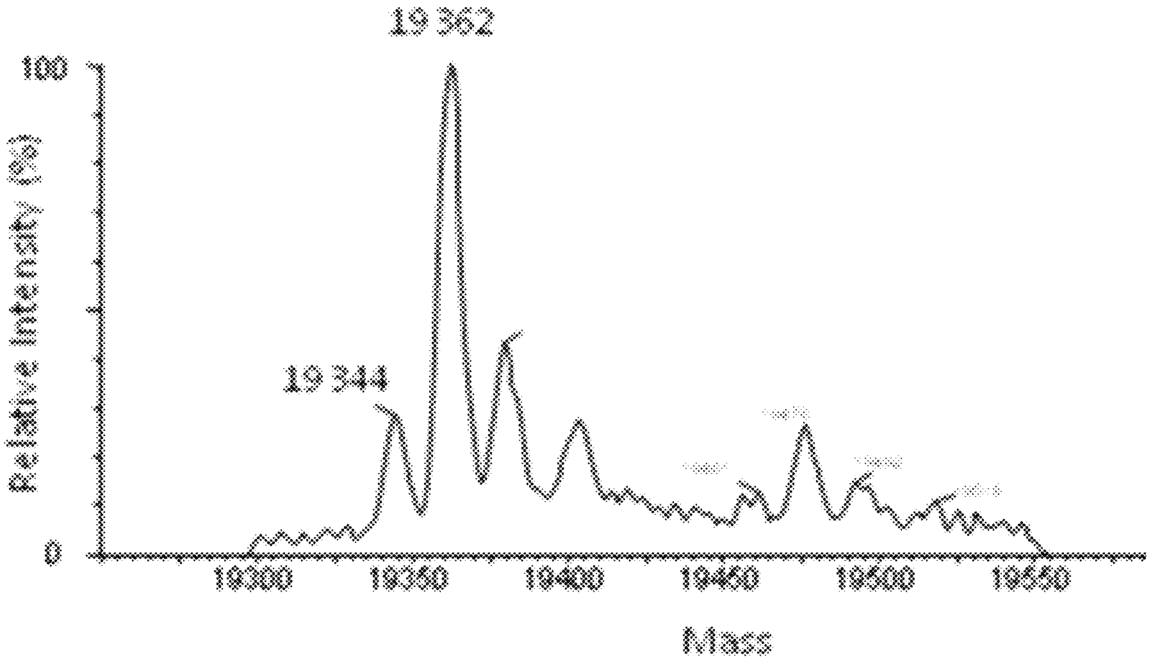
FIG. 4 denotes peptide mapping of hIFN alpha 2b including Nle substitution.

For further characterization, the sample was collected and subjected to trypsin/Lys-C LC-MS/MS peptide mapping. The modified tryptic peptides with −18 Da mass shift was searched against the parent peptides; and the sites of modification were confirmed by LC-MS/MS analysis (see FIG. 4). Table 2 below lists methionine-containing peptides exhibiting a mass shift of −18 Da compared to the respective parent peptides. Peptide MS/MS sequencing analysis identified that all mass shifts occur at the methionine residues. The data indicate that methionine residues was replaced with norleucine. In this example, the ratio between two Nle incorporation for Met 60 and Met 112 is about 1:1. Additionally, or alternatively, the ratio between Nle incorporation for Met 60 and Met 112 can be about 1:2, 1:3, 2:1, 3:1, or any variations thereof.

TABLE 2

| | | | | | % Nle Incorporation | |
|---|---|---|---|---|---|---|
| Peptide | Sequence Position | Theoretical Mass (Da) | Experimental Mass (Da) | Replacement Site | Enrichment in RP-HPLC Fractions | Final Overall Ratio |
| T8 | 51-71 | 2458.3 | 2458.3 | | | |
| Modified T8 | | 2440.3 | 2440.3 | Met 60 | 25.6 | 1 |
| T10 | 85-113 | 3301.6 | 3301.6 | | | |
| Modified T10 | | 3283.6 | 3283.7 | Met 112 | 9.2 | 1 |

Pro-IFN alfa-2b IEX-HPLC method also resolved Pro-IFN alfa-2b sample which contain substitution of Gly 45 leading to Asp and Asn 66 leading to Lys.

For amino acid substitution, two amino acid substitution have been identified in IEX-HPLC. Analysis showed that Pro-IFN alfa-2b contains amino acid substitution of Gly 45 to become Asp. Pro-IFN alfa-2b IEX-HPLC contains a Pro-IFN alfa-2b variant with substitution of Gly 45 leading to become Asp and Asn 66 to become Lys. Table 3 shows analysis of amino acid substituted peptides in IEX-HPLC.

TABLE 3

(pick Gly 45 to Asp or Asn 66 to Lys per application)

| Peptide | Sequence Position | Theoretical Mass (Da) | Experimental Mass (Da) | Site of Modification | Enrichment in IEX-HPLC | Final Overall Ratio |
|---|---|---|---|---|---|---|
| T6-7 | 33-50 | 2225.0 | 2225.0 | | | |
| Substitution T6-7 | | 2283.0 | 2283.0 | Gly 45 to Asp (Asp 45) | 45.9 | 1 |
| T7 | 35-50 | 1953.9 | 1953.9 | | | |
| Substitution T7 | | 2011.9 | 2011.9 | Gly 45 to Asp (Asp 45) | | |
| T8 | 51-71 | 2458.3 | 2458.3 | | | |
| Substitution T8 | 51-66 | 1896.0 | 1896.0 | Asn 66 to Lys (Lys66) | 25.3 | 5 |

Further quantitation showed that the ratio of amount of Gly 45 to Asp, and Asn 66 to Lys is about 1:5. Additionally, or alternatively, the ratio between the ratio amount of Gly 45 to Asp, and Asn 66 to Lys may be 1:1, 1:2, 1:3, 1:4, 2:1, 3:1, 4:1, 5:1 or any variation thereof.

CPE (Cytopathic Effect) assay showed the antiviral activity for old cell line derived Pro-IFN alfa-2b has a similar bioactivity (about $8.08E^{+08}$ IU/mg) when compared to the new cell line derived Pro-IFN alfa-2b (about $6.18E^{+08}$ IU/mg). The difference in bioactivity value is due to the wide variation of the CPE assay. All the above results showed that old cell line derived Pro-IFN alfa-2b are comparable to the new cell line derived Pro-IFN alfa-2b produced using modified manufacturing process.

Example 9

Multiple Runs

Figure 5:
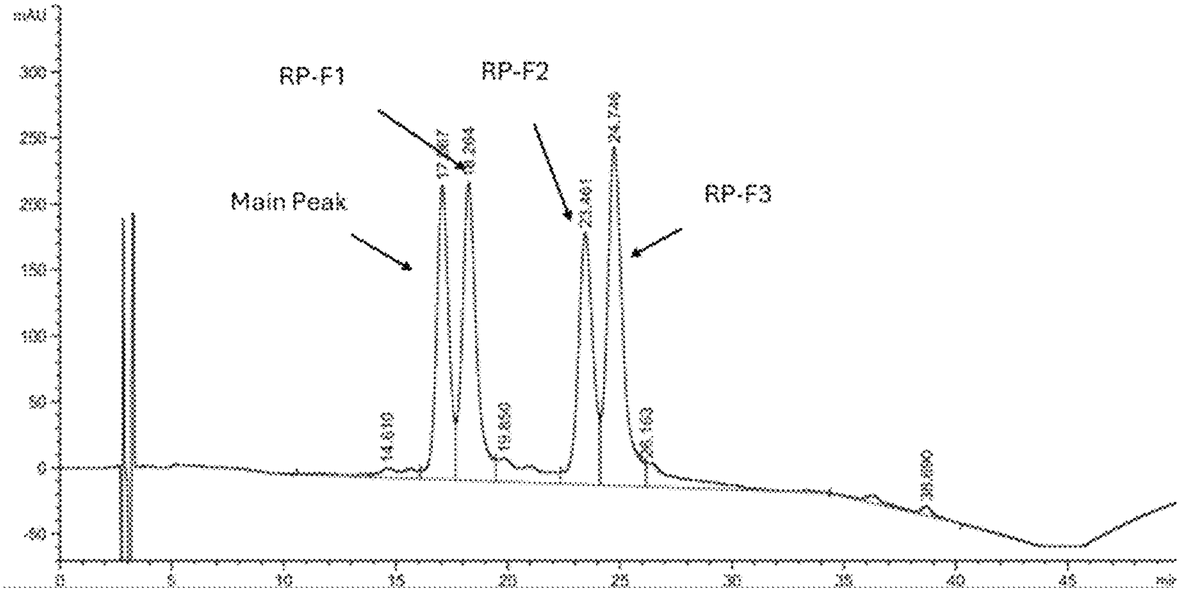
FIG. 5 denotes chromatography results with fraction peaks containing one or more substitution of this disclosure.
Figure 6:
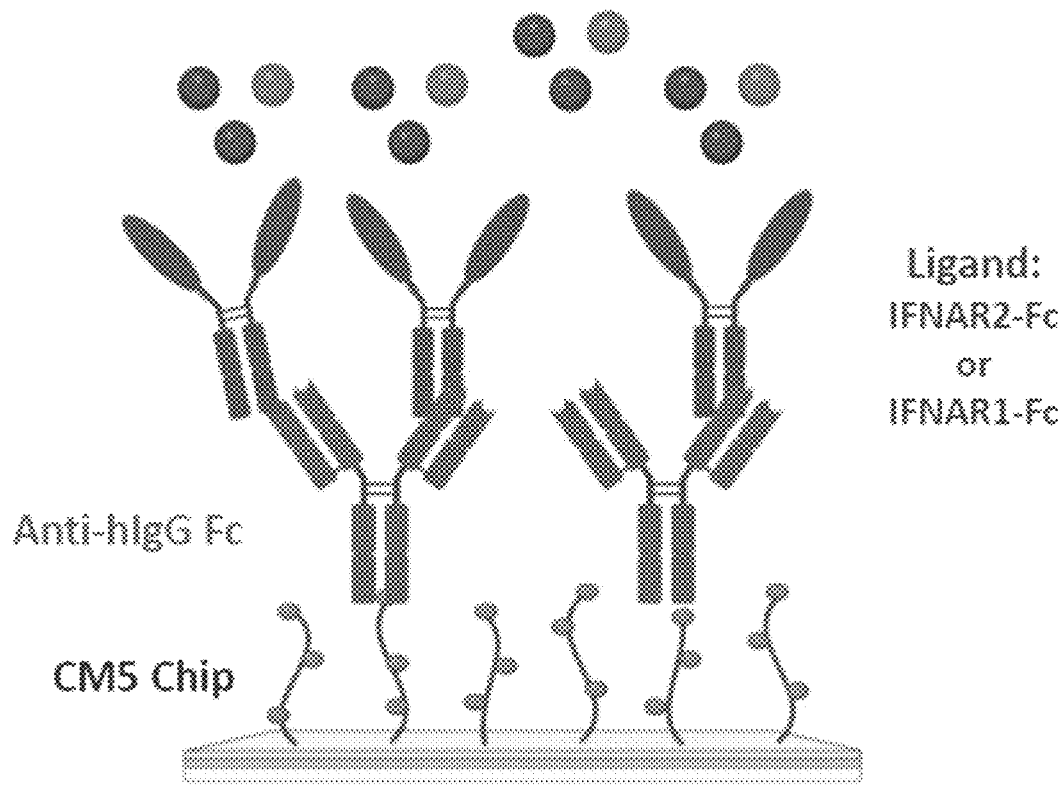
FIG. 6 denotes the multi-cycle kinetic analysis design (SPR) of modified hIFN alpha 2b (Pro-hIFN alpha 2b) molecule (also known as "analyte") to human IFNAR1-Fc/human IFNAR2-Fc.

The procedures from Examples 1-8 were repeated, with Nle added. After production and analysis, the chromatography results are denoted in FIG. 5 with 3 extra peaks relative to the main peak. The content of each peak was collected and further analyzed according to the procedures described above, and the additional Nle incorporated Pro-hIFN 2b results are denoted in Table 4.

TABLE 4

| Nle Modification | | Sample Name | | |
|---|---|---|---|---|
| Position | Peptide | F1 | F2 | F3 |
| 17 | T3 | 35.10% | 32.70% | 35.02% |
| 22 | T3 | 18.05% | 18.49% | 18.70% |
| 149 | T18 | 59.23% | 60.52% | 63.17% |

Here again, the mere fact that the detection of existence of Nle at Met 17, Met 22 and/or Met149 of Pro-hIFN alpha 2b in any ratio indicates the present the manufacturing method of the present disclosure, in part or in whole, was used.

In one of the multiple runs, the fermentation method was adjusted to perform a recombinant protein fermentation including the steps of: carrying out seeding (time $S_0$) of a culture of prokaryote host cell engineered to inducibly express a recombinant protein and transferring the culture into one or more fermenters each containing a culture medium; measuring a dissolved oxygen (DO) level, an agitation rate, and a pH in the one or more fermenters; supplying a carbon source feeding solution to any of the one or more fermenters individually, whenever condition(s) (i) and/or (ii) are met: (i) said DO level exceeds above about 35% to 45% and said agitation rate exceeds about 300 to 1,000 rpm; (ii) said agitation rate exceeds about 400 to 700 rpm and said pH exceeds about 7.0 to 7.4; and supplying a nitrogen source to any of the one or more fermenters in which induction of expression of the recombinant protein has been initiated, individually, at about $I_0$ (time at initiation of induction) or $I_1$ or both; optionally, supplying a nitrogen source to any of the one or more fermenters, individually, at one or more time points selected from about $S_5$, $S_6$, $S_7$, $S_8$, $S_9$ and $S_{10}$.

Here, the detection of Nle substitution and substitution of Gly 45 to Asp and Asn 66 to Lys Pro-hIFN alpha 2b was performed. The detection of the existence or of any amount of any of Nle substitution and/or substitution of Gly 45 to Asp and Asn 66 to Lys indicated the method of making Pro-hIFN alpha 2b disclosed in the present disclosure, in part of in whole, such as the above procedure and those disclosed in U.S. Patent Application Publication Number US20250101484A1 (the content of which are incorporated herein by reference in their entirely), was utilized, in whole or in part.

In another run, the composition produced included the quantitative ratio between Nle Met 17, Nle Met 22, and Nle Met 149 to be about 1:0.5:1.68, 1.76:1:3.27, 0.55:0.30:1, and/or any combinations/variation thereof. Further, the quantitative ratio between Asp substitution at position 45 and Lys substitution at position 66 can include about 1:1, 1:2, 1:3, 1:4, 2:1, 3:1, 4:1, 5:1, 1:5, and/or any variations thereof. The mere fact that the detection of existence of any substitution of Pro-hIFN alpha 2b in any ratio and/or the existence of amino acid substitution in any ratios thereof indicates the present the manufacturing method of the present disclosure, in part or in whole, was used.

In an aspect, the composition produced included the quantitative ratio between Nle Met 60, Nle Met 112, Nle Met 17, Nle Met 22, and Nle Met 149 to be about 1:30:11:5.7:18.8, 9.58:1:3.28:1.86:6.08, 5.2:4.96:1.87:1:3.37, and/or any combinations/variation thereof. Further, the quantitative ratio between Asp substitution at position 45 and Lys substitution at position 66 can include about 1:1, 1:2, 1:3, 1:4, 2:1, 3:1, 4:1, 5:1, 1:5 or any variations thereof. The mere fact that the detection of existence of any substitution of Pro-hIFN alpha 2b in any ratio and/or the existence of amino acid substitution in any ratios thereof indicates the present the manufacturing method of the present disclosure, in part or in whole, was used.

In one run, no Nle substituted and/or other amino acid substituted Pro-IFN A2b is reported.

Example 10

SPR Analysis

In this example, the ligand human IFNAR1-Fc/human IFNAR2-Fc was captured on the surface of a Sensor Chip Protein A. The multi-cycle kinetic analysis of control, analyte 1, 2, and 3 to human IFNAR1-Fc/human IFNAR2-Fc were performed by using Biacore T200.

Human IFNAR1-Fc/human IFNAR2-Fc was first diluted with 1×HBS-EP+ to obtain a final concentration of 8 μg/ml and captured by flow cell 2 of a Sensor Chip Protein A. The chip contains MabSelect SuRe ligand on the surface, allowing orientation-specific binding of the Fc region of an antibody.

The assay was performed by using the Kinetic/Affinity wizard. The flow path was 2-1, as the ligand was injected and captured in flow cell 2, and flow cell 1 acted as a reference. A series of concentrations of analyte 1-3 were injected over the reference and the ligand surfaces consecutively as the association phase, with short dissociation phases in between by injecting running buffer. Then, regeneration solution was injected as the regeneration phase. All the procedures were conducted at 25° C. One of the fermentation run was produced under conditions with addition of 6 mM norleucine solution (44 μg/L L-norleucine and 166.7 μg/L formic acid). The resulting KD are shown in Table 5 below.

TABLE 5

| | Analyte | | | Pro-hIFN a2b | Analyte 1 | Analyte 2 | Analyte 3 |
|---|---|---|---|---|---|---|---|
| Ligand | human IFNAR1-Fc | Steady-state affinity model analysis | KD (M) | 3.14E−06 | 2.33E−06 | 2.00E−06 | 1.71E−06 |
| | human IFNAR2-Fc | Kinetic 1:1 binding model analysis | KD (M) | 1.49E−09 | 2.37E−09 | 2.29E−09 | 2.20E−09 |

Briefly in sum, as observed above, norleucine substitution did not show any significant difference in binding affinity compared to control (Pro-hIFN a2b).

It is contemplated that any embodiment discussed in this specification can be implemented with respect to any method, kit, reagent, or composition of the disclosure, and vice versa. Furthermore, compositions of the disclosure can be used to achieve methods of the disclosure.

It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What we claim are:

1. An amino acid substituted Pro-hIFN alpha 2b composition comprising a Nle substitution at position 17 in SEQ ID NO: 1, a Nle substitution at position 22 in SEQ ID NO: 1, and a Nle substitution at position 149 in SEQ ID NO: 1.

2. The composition according to claim 1, further comprising an amino acid substitution of Asp at position 45 from Gly or an amino acid substitution of Lys at position 66 from Asn.

3. The composition according to claim 1, further comprising an amino acid substitution of Asp at position 45 from Gly, and an amino acid substitution of Lys at position 66 from Asn.

* * * * *

SEQUENCE LISTING

```
Sequence total quantity: 2
SEQ ID NO: 1            moltype = AA  length = 165
FEATURE                 Location/Qualifiers
source                  1..165
                        mol_type = protein
                        organism = Synthetic construct
SEQUENCE: 1
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 2            moltype = AA  length = 166
FEATURE                 Location/Qualifiers
source                  1..166
                        mol_type = protein
                        organism = Synthetic construct
```

-continued

```
SEQUENCE: 2
PCDLPQTHSL GSRRTLMLLA QMRRISLFSC LKDRHDFGFP QEEFGNQFQK AETIPVLHEM  60
IQQIFNLFST KDSSAAWDET LLDKFYTELY QQLNDLEACV IQGVGVTETP LMKEDSILAV  120
RKYFQRITLY LKEKKYSPCA WEVVRAEIMR SFSLSTNLQE SLRSKE                 166
```